*(12)* United States Patent
Prough et al.

*(10)* Patent No.: US 12,076,138 B2
*(45)* Date of Patent: Sep. 3, 2024

(54) ULTRASOUND-GUIDED OPTOACOUSTIC MONITORING OF OXYGEN SATURATION

(71) Applicant: Board of Regents, The University of Texas System, Austin, TX (US)

(72) Inventors: Donald S. Prough, Galveston, TX (US); Michael P Kinsky, League City, TX (US); Rinat O. Esenaliev, Galveston, TX (US); Irene Y. Petrov, Galveston, TX (US); Yuriy Petrov, Galveston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 445 days.

(21) Appl. No.: 16/332,538

(22) PCT Filed: Sep. 12, 2017

(86) PCT No.: PCT/US2017/051217
§ 371 (c)(1),
(2) Date: Mar. 12, 2019

(87) PCT Pub. No.: WO2018/049415
PCT Pub. Date: Mar. 15, 2018

(65) Prior Publication Data
US 2019/0231239 A1    Aug. 1, 2019

Related U.S. Application Data

(60) Provisional application No. 62/393,520, filed on Sep. 12, 2016.

(51) Int. Cl.
*A61B 5/00*     (2006.01)
*A61B 5/145*    (2006.01)
(Continued)

(52) U.S. Cl.
CPC ........ *A61B 5/14542* (2013.01); *A61B 5/0095* (2013.01); *A61B 5/145* (2013.01); *A61B 8/0891* (2013.01); *A61B 8/4281* (2013.01)

(58) Field of Classification Search
CPC ... A61B 5/0095; A61B 5/145; A61B 5/14542; A61B 8/0891; A61B 8/4281
See application file for complete search history.

(56) References Cited

U.S. PATENT DOCUMENTS 6,498,942 B1 * 12/2002 Esenaliev ............ A61B 5/0095
                                                     600/310
6,751,490 B2    6/2004 Esenaliev et al.
(Continued)

FOREIGN PATENT DOCUMENTS

JP          3127252 B2      1/2001
JP       2011172730 A       9/2011
(Continued)

OTHER PUBLICATIONS

Office Action dated Jul. 7, 2020 issued in counterpart Japanese Patent Application No. 2019-514843.
Office Action dated Dec. 3, 2020 in counterpart Canadian Patent Application No. 3,036,376.
Rivers, Emanuel et al. "Early Goal-Directed Therapy in the Treatment of Severe Sepsis and Spetic Shock." The New England Journal of Medicine, vol. 345, No. 19, Nov. 8, 2001, pp. 1368-1377.
International Search Report dated Nov. 13, 2017 in Counterpart PCT application No. PCT/US2017/051217.
(Continued)

*Primary Examiner* — Amelie R Davis
(74) *Attorney, Agent, or Firm* — Thomas | Horstemeyer, LLP

(57) ABSTRACT

Apparatus and methods are described for ultrasound guided optoacoustic monitoring to provide diagnostic information for many clinical applications blood oxygenation in blood vessels and in tissues including for early diagnosis and management of circulatory shock (including that induced by hemorrhage). In certain embodiments provided herein, methods and apparatus for optoacoustics for measurement of blood oxygenation in the innominate vein are provided.

11 Claims, 20 Drawing Sheets

(51) Int. Cl.
  *A61B 8/00* (2006.01)
  *A61B 8/08* (2006.01)

(56) References Cited

U.S. PATENT DOCUMENTS

| | | | |
|---|---|---|---|
| 2004/0236224 A1 | 11/2004 | Stringer et al. | |
| 2004/0254460 A1* | 12/2004 | Burcher | A61B 5/6843 600/437 |
| 2005/0187471 A1* | 8/2005 | Kanayama | A61B 5/0091 600/437 |
| 2006/0253007 A1* | 11/2006 | Cheng | A61B 5/14551 600/310 |
| 2008/0071172 A1 | 3/2008 | Bruck et al. | |
| 2008/0255433 A1 | 10/2008 | Prough et al. | |
| 2010/0022888 A1* | 1/2010 | George | A61B 8/4209 600/459 |
| 2011/0088477 A1* | 4/2011 | Someda | A61B 5/0035 73/641 |
| 2011/0230750 A1* | 9/2011 | Tateyama | A61B 8/14 600/407 |
| 2013/0172703 A1* | 7/2013 | Dixon | A61B 5/14552 600/339 |
| 2013/0190595 A1 | 7/2013 | Oraevsky et al. | |
| 2013/0322204 A1* | 12/2013 | Ebisawa | A61B 5/0095 367/7 |
| 2014/0073900 A1* | 3/2014 | Wood | A61B 5/14551 600/407 |
| 2014/0275943 A1* | 9/2014 | Kang | A61B 5/08 600/407 |
| 2016/0058289 A1* | 3/2016 | Shigeta | A61B 5/0095 600/407 |
| 2017/0143278 A1* | 5/2017 | Nakamura | A61B 5/742 |

FOREIGN PATENT DOCUMENTS

| | | | |
|---|---|---|---|
| JP | 2013048739 A | | 3/2013 |
| JP | 2013255707 A | | 12/2013 |
| JP | 2016067491 A | | 5/2016 |
| WO | 2016007678 A1 | | 1/2016 |
| WO | WO 2016/051749 | * | 4/2016 |

OTHER PUBLICATIONS

Petrov, Irene Y. et al. "Optoacoustic Measurement of Central Venous Oxygenation for Assessment of Circulatory Shock: Clinical Study in Cardiac Surgery Patients." Progress in Biomedical Optics and Imaging, SPIE—International Society for Optical Engineering, Bellingham, WA, US, vol. 8943, Mar. 3, 2014, pp. 1-5.

Petrov, Andrey et al. "Optoacoustic Monitoring of Central and Peripheral Venous Oxygenation During Simulated Hemorrhage." Progress in Biomedical Optics and Imaging, SPIE—International Society for Optical Engineering, Bellingham, WA, US, vol. 8943, Mar. 3, 2014, pp. 1-6.

Haisch, C. et al. "OPUS—Optoacoustic Imaging Combined with Conventional Ultrasound for Breast Cancer Detection." Progress in Biomedical Optics and Imaging, SPIE—Novel Optical Instrumentation for Biomedical Applications III 2007 SPIE, US, vol. 6631, Jan. 1, 2007, pp. 1-14.

Petrov, Yuriy et al. "Combination of Optoacoustics and Ultrasound Imaging for Non-Invasive, Rapid Assessment and Management of Circulatory Shock." Photons Plus Untrasound: Imaging and Sensing 2011, SPIE, 1000 20th St. Bellinghan WA, 98225-6705 USA, vol. 7899, No. 1, Feb. 10, 2011, pp. 1-5.

Petrov, Irene Y. et al. "High-Resolution Ultrasound Imaging and Noninvasive Optoacoustic Monitoring of Blood Variables in Peripheral Blood Vessels." Photons Plus Ultrasound: Imaging and Sensing 2011, SPIE, 1000 20th St. Bellingham WA, 98225-6705 USA, vol. 7899, No. 1, Feb. 10, 2011, pp. 1-5.

Search Report dated Mar. 11, 2020 in counterpart European Patent Application 17849788.9.

Office Action dated Sep. 14, 2022 in co-pending Canadian Application No. 3,036,376 filed Sep. 12, 2017.

Office Action dated Nov. 19, 2022 for Japanese Patent Application No. 2021-202337.

Petrov, Irene Y., et al. "Optoacoustic measurement of central venous oxygenation for assessment of circulatory shock: clinical study in cardiac surgery patients." Photons Plus Ultrasound: Imaging and Sensing 2014. vol. 8943. SPIE, 2014.

Examination Report No. 1 dated Apr. 18, 2023 for Australian Patent Application No. 2022200850.

* cited by examiner

*Fig. 1A*
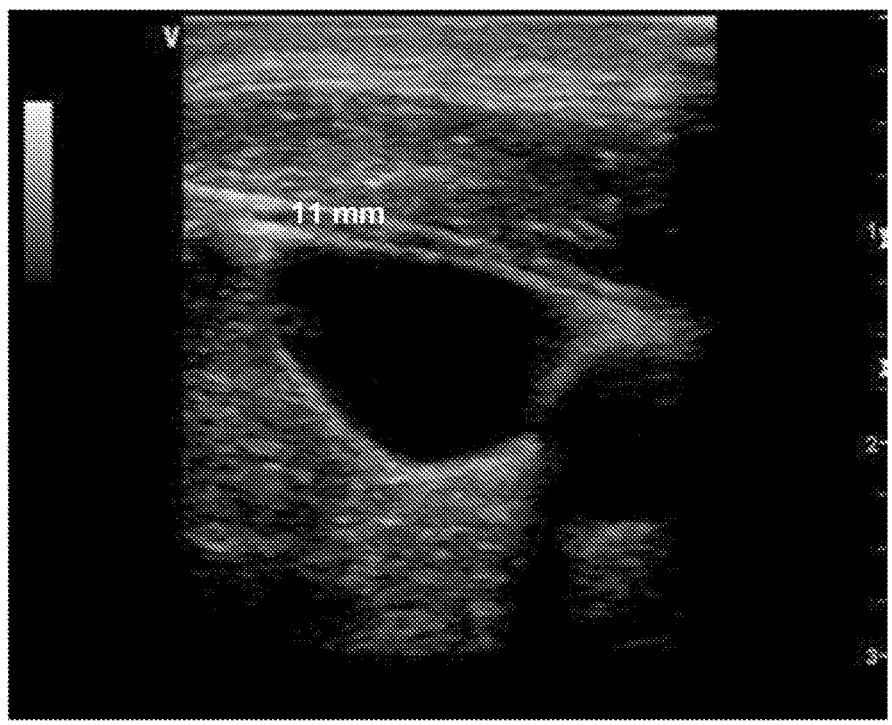
*Fig. 1B*
*Fig. 1C*
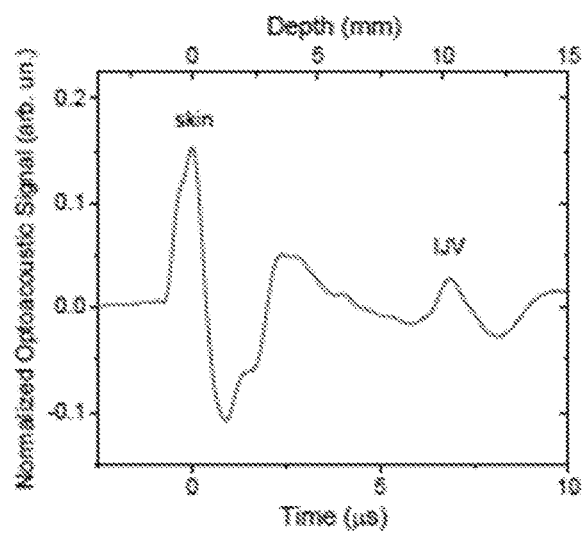
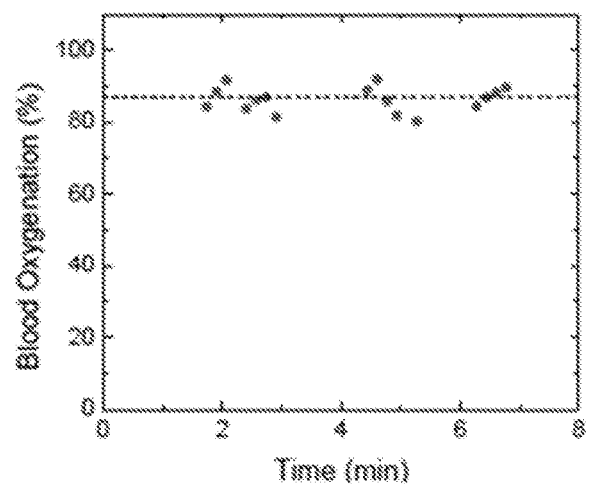

Left Innominate Vein (LIV)

Noninvasive, optoacoustic monitoring with the laser diode system (subject 9)
Innominate vein oxygenation Noninvasive, optoacoustic monitoring with the laser diode system (subject – 9): internal jugular vein oxygenation Noninvasive, optoacoustic monitoring with the laser diode system (subject 9): External jugular vein oxygenation

Fig. 11

Hemorrhage Classification – Use of Venous Oxygenation

| Class | Blood loss | Venous oxygenation | | Gradient | Treatment |
|---|---|---|---|---|---|
| NML | 0 | $S_{IJV}O_2$ = 70-80%<br>$S_{InV}O_2$ = 70-80% | | zero | none |
| I | <15 %(0.75 l) | $S_{IJV}O_2$ = 70-80%<br>$S_{InV}O_2$ = 50-60% | | ↑ | minimal |
| II | 15-30 %(0.75-1.5 l) | $S_{IJV}O_2$ = 70-80%<br>$S_{InV}O_2$ = 40-50% | | ↑↑ | intravenous fluids |
| III | 30-40 %(1.5-2 l) | $S_{IJV}O_2$ = 50-70%<br>$S_{InV}O_2$ = 30-50% | | ↑ | fluids and packed RBCs |
| IV | >40 %(>2 l) | $S_{IJV}O_2$ = 30-50%<br>$S_{InV}O_2$ = 30-40% | | zero | Shock: aggressive intervention |

$SvO_2\ _{IJV}$ = oxygen saturation of internal jugular vein
$SvO_2\ _{InV}$ = oxygen saturation of innominate vein
Gradient = $[S_{IJV}O_2] - [S_{InV}O_2]$

*Fig. 12*

Fig. 13A
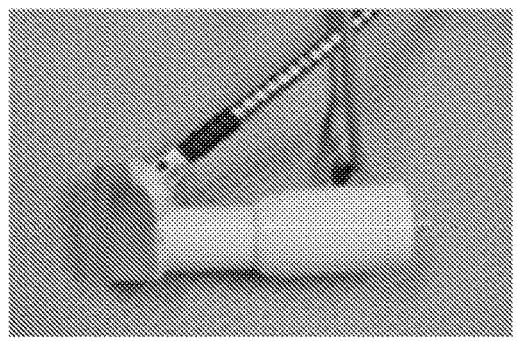
Fig. 13B
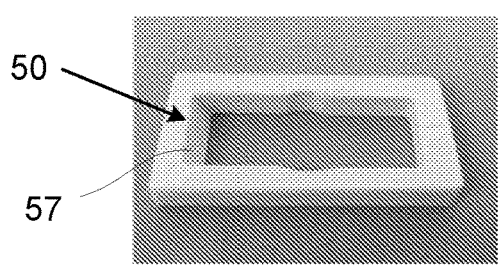
Fig. 13C    Top View
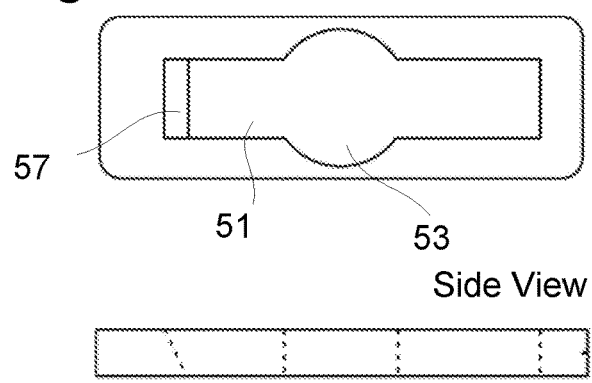
Side View
Fig. 13D
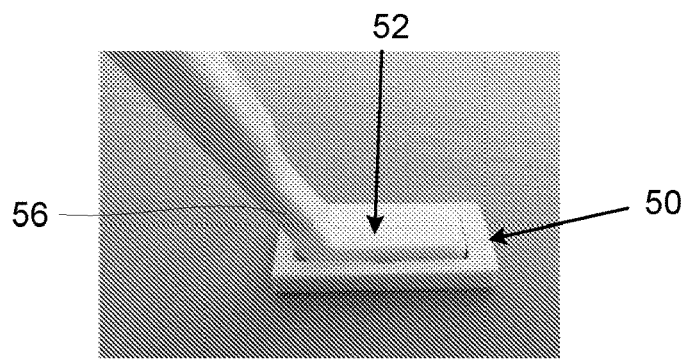
Fig. 13E
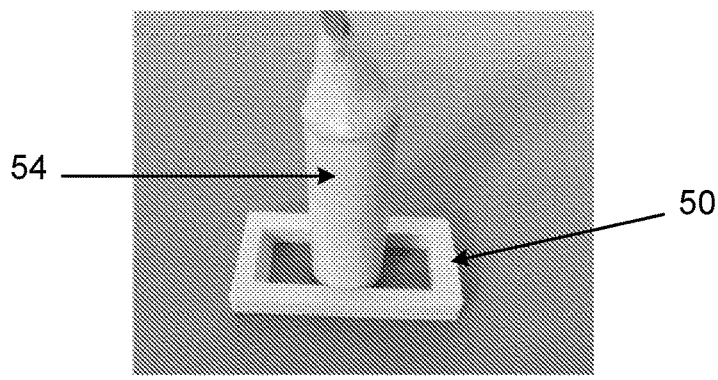

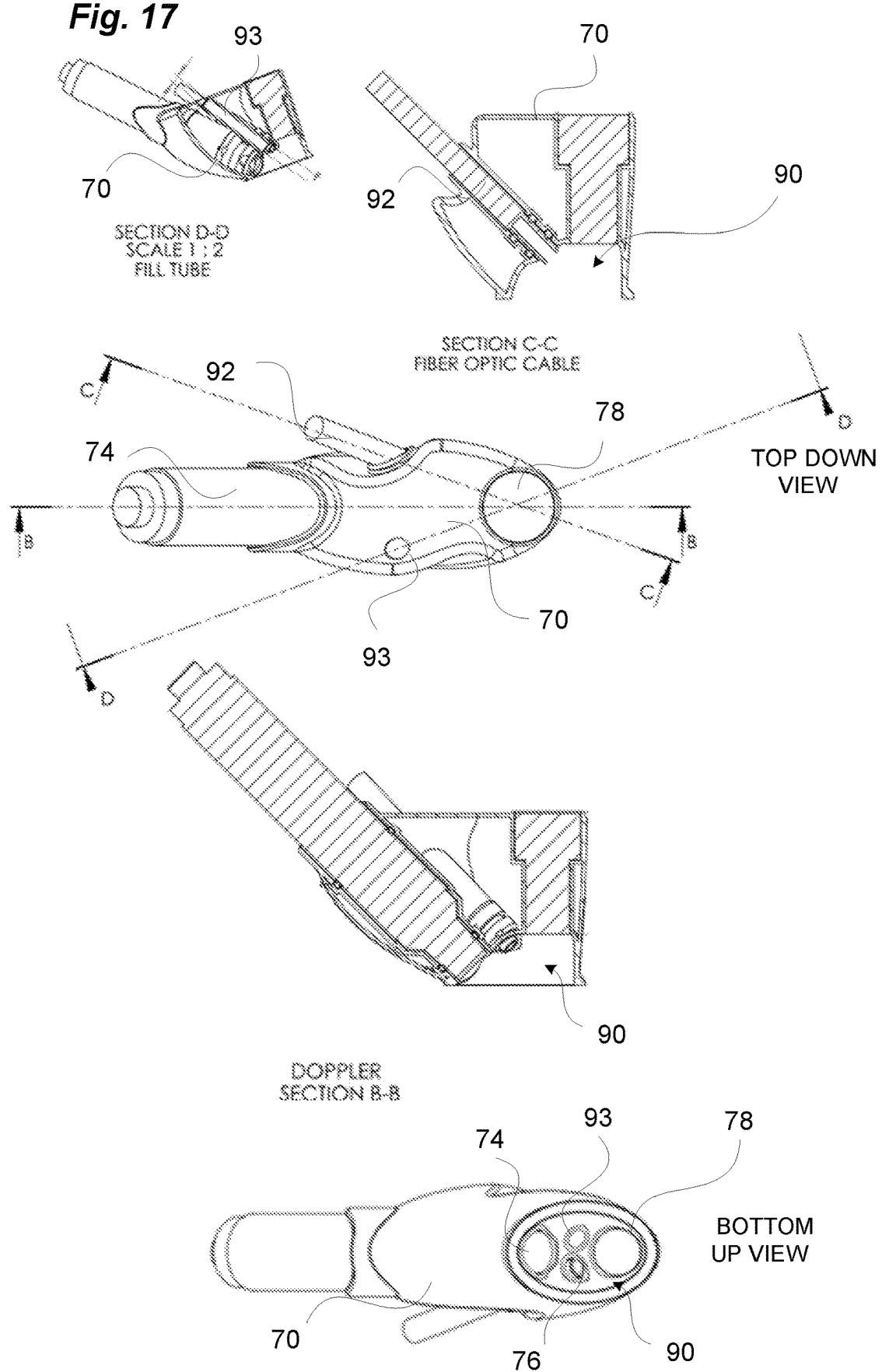

ULTRASOUND-GUIDED OPTOACOUSTIC MONITORING OF OXYGEN SATURATION

REFERENCE TO RELATED APPLICATIONS

This application claims priority based on PCT/US17/51217, filed Sep. 12, 2017, which in turn claims priority based on U.S. Provisional Application Ser. No. 62/393,520, filed Sep. 12, 2016, each of which are incorporated herein by reference in their entireties.

FIELD OF THE INVENTION

This invention relates generally to apparatus and methods for measurement of blood oxygenation in the major veins.

BACKGROUND OF THE INVENTION

Without limiting the scope of the invention, its background is described in connection with existing methods for measurement of blood oxygenation in major veins and in particular the innominate or brachiocephalic vein.

Civilian trauma is similar to military trauma with leading cause of death and morbidity is due to hemorrhage with and without traumatic brain injury (TBI). Potentially survivable injuries from hemorrhage require rapid assessment and treatment. Prompt triage from point of injury to definitive care has been shown to improve outcome. However, rapid triage is rarely feasible in combat casualty care. Thus, improvements in prolonged field care (PFC), which is up to 72 hr combat casualty care in austere environments, are essential. Potentially lethal injuries, e.g. hemorrhage with and without TBI, must be effectively managed during this prolonged and critical period, which necessitates precise resuscitation in order to prevent sequelae of over- and under-resuscitation. The use of vital signs, e.g., blood pressure, etc., to guide resuscitative efforts in hemorrhage have poor predictive value, especially in the young and healthy. TBI in combination with hemorrhage can further confound vital sign interpretation. This is especially problematic since hypovolemia dramatically worsens outcome in TBI victims.

Outcomes are dramatically worsened if TBI is not recognized. Currently, the primary indices used to diagnose and monitor treatment of hemorrhagic shock are blood pressure, heart rate, and mental status, which are relatively nonspecific and insensitive. Further, those indices could be relatively normal despite ongoing tissue hypoperfusion. No rapidly available noninvasive diagnostic test is available to detect systemic hypoperfusion in patients in whom blood pressure and heart rate are grossly normal.

Although supplemental monitoring can detect tissue hypoperfusion and guide resuscitation efforts, the only measurement shown to improve outcome in circulatory shock is central venous (superior vena cava (SVC)) hemoglobin saturation ($S_{SVC}O_2$). Early goal-directed therapy (EGDT) resuscitation of hypovolemic septic shock, guided by targeting $S_{SVC}O_2$, Rivers and colleagues reduced both mortality (46.5% to 30.5%) and hospitalization cost. See Rivers E, et al. Early Goal-Directed Therapy in the Treatment of Severe Sepsis and Septic Shock. *N Engl J Med.* 345 (2001) 1368-1377. $S_{SVC}O_2$ has also been proposed as a prognostic indicator in several pathological conditions, including polytrauma patients. Low $S_{SVC}O_2$ in major trauma and head injury patients was associated with higher mortality and prolonged hospitalization. Measuring $S_{SVC}O_2$ in the critical interval from point-of-injury to definitive care would improve diagnosis of early shock and enable monitoring of therapeutic interventions. However, central venous catheterization is invasive, time-consuming, complication-prone and challenging in resource-constrained conditions.

From the foregoing, it appeared to the present inventors that apparatus and methods for non-invasive monitoring of $SO_2$ would provide a long needed solution to support and direct EGDT.

SUMMARY OF THE INVENTION

Provided herein are methods and apparatus for ultrasound guided optoacoustic measurement of blood oxygenation in a blood vessel. In certain embodiments a site for monitoring the blood vessel is first identified using an ultrasound probe, and subsequently, an optoacoustic stimulus and detector is utilized at the identified site and blood oxygenation is measured in venous blood carried by the blood vessel using the optoacoustic stimulus and detector. In certain embodiments, the blood vessel is selected from the innominate vein, the internal jugular vein, the subclavian vein and the femoral vein.

In particular embodiments the blood vessel is the innominate vein. In certain embodiments the site is located using a patient interface through which the ultrasound probe is first removably applied to locate the blood vessel followed by removal of the ultrasound probe and application of the optoacoustic probe. In other embodiments, the ultrasound probe and the optoacoustic stimulus and detector are mounted together in a holder and once the blood vessel of interest is located with the ultrasound probe, optoacoustic stimulation is delivered and measurements are performed with the optoacoustic detector. In such embodiments the ultrasound locating and optoacoustic measuring may be performed simultaneously and continuously.

In certain embodiments of the method an axis of the optoacoustic stimulus is parallel to an axis of the ultrasound probe while in other embodiments an axis of the optoacoustic stimulus is adjusted at an angle with respect to an axis of the ultrasound probe to provide accurate probing from a specific depth in the blood vessel.

In certain embodiments, the ultrasound locating and optoacoustic measuring are performed using the same ultrasound probe.

In certain embodiments, the optoacoustic stimulus is provided with at least a pair of wavelengths selected from: 760 nm and 800 nm; 1064 nm and 800 nm; and 760 nm and 1064 nm.

In certain embodiments, a patient interface for ultrasound guided optoacoustic measurement of blood oxygenation in a blood vessel is provided including a holder that is dimensioned to securely hold an ultrasound probe, and a subsequently applied optoacoustic probe to a site on a patient where the ultrasound probe is able to detect a major vein and the optoacoustic probe is able to detect blood oxygenation in the detected major vein.

In other embodiments an apparatus for ultrasound guided optoacoustic measurement of blood oxygenation in a blood vessel is provided that includes a housing that is dimensioned to securely and simultaneously hold an ultrasound probe, an optoacoustic probe, and a light source for generating optoacoustic waves at a site on a patient where the ultrasound probe is able to detect a major vein and the optoacoustic probe is able to detect blood oxygenation in the detected major vein. The housing may further include a gel cavity that is adapted to hold an acoustic gel that directly communicates a face of the ultrasound probe and face of the optoacoustic probe to a skin of a patient. In certain embodiments, the housing includes a gel fill tube that provides for filling and maintaining a fill of the gel cavity. The housing may directs an axis of the ultrasound probe and an axis of the optoacoustic probe in parallel or at an angle to each other. The light source may be an optical parametric oscillator (OPO), laser diode, light emitting diode (LED), pulsed laser diode, dye laser, or solid state laser while the optoacoustic probes may include a piezodetector that is based on piezomaterials selected from piezopolymers and piezoceramics, capacitive micromachined ultrasonic transducers (CMUTs), and optically-based ultrasound detectors including interferometric detectors, optical beam deflecting detectors, pressure-sensitive optical elements.

Further provided herein are clinical validation protocols to establish efficacy of a device and method for ultrasound guided optoacoustic monitoring of oxygen saturation comprising testing a combination ultrasound and optoacoustic apparatus using lower body negative pressure ("LBNP"). In certain embodiments the clinical validation protocol of compares optoacoustically monitored $S_{LIV}O_2$ to oxygenation of subclavian vein blood, obtained from an oximetric pulmonary artery ("PA") catheter infusion port.

BRIEF DESCRIPTION OF THE DRAWINGS

For a more complete understanding of the present invention, including features and advantages, reference is now made to the detailed description of the invention along with the accompanying figures:

FIG. 1A shows an ultrasound image of the right internal jugular vein of a sheep. The optoacoustic probe was placed on the anterior neck surface and measured for optoacoustic oxygenation. FIG. 1B shows the optoacoustic signal obtained from the IJV at the 10-11 mm point shown in FIG. 1A. FIG. 1C shows optoacoustic determination of venous oxygen at 82±2% versus 83% via co-oximetry [dashed line].

FIG. 3A indicates more anatomical features while in FIG. 3B certain features are not shown to provide a clearer depiction.

FIG. 4B shows Pulse wave Doppler, positioned on center of LIV and demonstrates a low frequency venous pulse waveform (5) that varied with respiration.

FIGS. 6A-6B show data for the left innominate vein with FIG. 6A showing blood oxygenation values and FIG. 6B showing the optoacoustic signal with depth through the tissue.

FIGS. 7A-7B show data for the internal jugular vein with FIG. 7A showing blood oxygenation values and FIG. 7B showing the optoacoustic signal with depth through the tissue.

FIGS. 8A-8B show data for the external jugular vein with FIG. 8A showing blood oxygenation values and FIG. 8B showing the optoacoustic signal with depth through the tissue.

FIG. 9A shows a side view of the elongated profile and FIG. 9B shows that the skin contact surface is a small rectangular face.

FIG. 11 depicts hemorrhage classifications based on determinations of venous oxygenation.

FIG. 12 depicts an example of a confirmatory human protocol utilizing progressive LBNP.

FIG. 13A-FIG. 13E depict sequential usage of U/S and optoacoustic probes. FIG. 13A shows one example of an optoacoustic probe. FIG. 13B-FIG. 13D show an example of use of a holder that controls the positioning of both U/S and optoacoustic probes sequentially. FIG. 13B depicts an image of a holder prototype, the geometry which allows for inserting ultrasound and optoacoustic probes. FIG. 13C depicts a drawing of top and side views of the holder shown in FIG. 13B. FIG. 13E depicts the optoacoustic probe inserted in the holder.

FIG. 17 depicts another embodiment of a dual ultrasound (or Doppler) probe and an optoacoustic probe.

DETAILED DESCRIPTION OF THE INVENTION

Figure 2A:
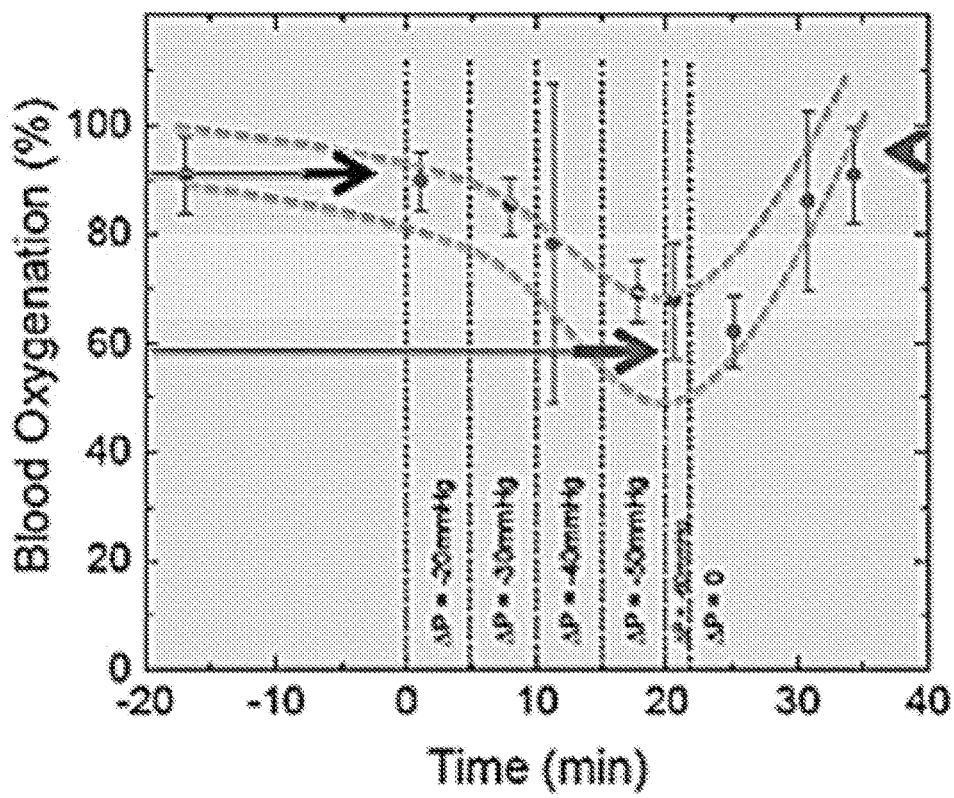
FIG. 2A shows determinations of blood oxygenation optoacoustically measured over the BV during a Lower Body Negative Pressure (LBNP) study.

Provided herein is a unique, noninvasive method of optoacoustic measurement of $SO_2$ in major veins to facilitate rapid diagnosis and treatment of circulatory shock with and without TBI. Venous oxygen (hemoglobin) saturation ($SO_2$) is a single, easily interpreted number that represents systemic and local factors that influence systemic oxygen delivery ($DO_2$) and oxygen consumption ($VO_2$). However, existing assessment of venous saturation is invasive. Presently such measurements must be made by continuous oximetric catheters for the pulmonary artery ("PA") (providing mixed venous $SO_2$), jugular bulb (providing brain $SO_2$) or the superior vena cava ("SVC"), and require invasive catheterization, which is risky and consumptive.

In certain embodiments, measurement of $SO_2$ in the left innominate vein ($S_{LIV}O_2$) provides rapid diagnosis and treatment of circulatory shock with and without TBI. The left innominate vein, also known as the brachiochephalic vein, collects venous blood from the jugular vein and is the main venous tributary for the superior vena cava and is thus a primary vessel for measuring and monitoring $SO_2$ in the venous brain drainage. The noninvasive optoacoustic measurement of $S_{LIV}O_2$ disclosed herein provides rapid recognition of occult hemorrhagic shock and subsequently provides resuscitation monitoring such that over-resuscitation is less likely. The technology is particularly valuable during prolonged field care, while awaiting evacuation. Based upon evidence of continued or previously unrecognized hemorrhage enabled by the technology disclosed herein, a combat or civilian medic could initiate fluid resuscitation to maintain adequate perfusion during the interval before definitive control of hemorrhage can be achieved.

In certain embodiments, algorithms for use of $S_{LIV}O_2$ data generated using the methods and apparatus disclosed herein will resemble those used with invasive SVC oximetry. For instance, Rivers et al. used a threshold of <70% saturation to define the need for interventions such as fluid or blood administration or inotropic infusions. See Rivers, et al. supra. Low $S_{LIV}O_2$ can be used in exactly the same way, with the exception that $S_{LIV}O_2$ can be measured noninvasively within one minute even during ambulance or helicopter transport, whereas central venous oximetry requires central venous catheterization and generally is not practical until a patient is stabilized in a hospital. $S_{LIV}O_2$ monitoring is also easily incorporated into automated decision-support or closed-loop management systems as these evolve for use in civilian trauma patients.

Ultrasound guided optoacoustic monitoring is expected to provide valuable diagnostic information for many clinical applications. One of them is optoacoustic monitoring of blood variables as such as blood oxygenation in blood vessels and in tissues. Ultrasound-guided optoacoustic monitoring of central venous oxygenation can be used for early diagnosis and management of circulatory shock (including that induced by hemorrhage). Either standard ultrasound imaging or Doppler technology, or both can be used for guidance of optoacoustic probe to perform targeted probing of specific blood vessels and measurement of blood oxygenation. Ultrasound guidance to locate the large vein for oxygenation can be performed in a number of modes including:

In certain embodiments provided herein, methods and apparatus for optoacoustics for measurement of blood oxygenation in the innominate vein. Ultrasound imaging and Doppler techniques provide important information on location of this blood vessel.

While the making and using of various embodiments of the present invention are discussed in detail below, it should be appreciated that the present invention provides many applicable inventive concepts which can be employed in a wide variety of specific contexts. The specific embodiment discussed herein are merely illustrative of specific ways to make and use the invention and do not delimit the scope of the invention.

ABBREVIATIONS

The following abbreviations are used throughout this application:
BV Basilic Vein
$DO_2$ Oxygen Delivery
IJV Internal Jugular Vein
LBNP Lower Body Negative Pressure
LIV Left Innominate Vein
NIR Near-Infrared
PA Pulmonary Artery
PEEP Positive End-Expiratory Pressure
PFC Prolonged Field Care
PLD Pulsed Laser Diodes
PZT Piezoceramic lead zirconate titanate ($Pb[Zr_{(x)}Ti_{(1-x)}]O_3$)
PVDF piezopolymer polyvinylidene fluoride
$S_{LIV}O_2$ Oxygen Saturation measured at the LIV
$SO_2$ Venous hemoglobin or oxygen saturation
$S_{PA}O_2$ mixed venous oxygen saturation by invasive pulmonary artery catheterization
$S_{SSs}O_2$ Oxygen saturation measured at the Superior Sagittal Sinus
SVC Superior Vena Cava
$S_vO_2$ mixed venous saturation
TBI Traumatic Brain Injury
U/S Ultrasound
$VO_2$ oxygen consumption To facilitate the understanding of this invention, and for the avoidance of doubt in construing the claims herein, a number of terms are defined below. Terms defined herein have meanings as commonly understood by a person of ordinary skill in the areas relevant to the present invention. The terminology used to describe specific embodiments of the invention does not delimit the invention, except as outlined in the claims.

The terms such as "a," "an," and "the" are not intended to refer to a singular entity unless explicitly so defined, but include the general class of which a specific example may be used for illustration. The use of the terms "a" or "an" when used in conjunction with "comprising" in the claims and/or the specification may mean "one" but may also be consistent with "one or more," "at least one," and/or "one or more than one."

The use of the term "or" in the claims is used to mean "and/or" unless explicitly indicated to refer to alternatives as mutually exclusive. Thus, unless otherwise stated, the term "or" in a group of alternatives means "any one or combination of" the members of the group. Further, unless explicitly indicated to refer to alternatives as mutually exclusive, the phrase "A, B, and/or C" means embodiments having element A alone, element B alone, element C alone, or any combination of A, B, and C taken together.

Similarly, for the avoidance of doubt and unless otherwise explicitly indicated to refer to alternatives as mutually exclusive, the phrase "at least one of" when combined with a list of items, means a single item from the list or any combination of items in the list. For example, and unless otherwise defined, the phrase "at least one of A, B and C," means "at least one from the group A, B, C, or any combination of A, B and C." Thus, unless otherwise defined, the phrase requires one or more, and not necessarily not all, of the listed items.

The terms "comprising" (and any form thereof such as "comprise" and "comprises"), "having" (and any form thereof such as "have" and "has"), "including" (and any form thereof such as "includes" and "include") or "containing" (and any form thereof such as "contains" and "contain") are inclusive or open-ended and do not exclude additional, unrecited elements or method steps.

The term "effective" as used in the specification and claims, means adequate to provide or accomplish a desired, expected, or intended result. The terms "about" or "approximately" are defined as being close to as understood by one of ordinary skill in the art, and in one non-limiting embodiment the terms are defined to be within 10%, within 5%, within 1%, and in certain aspects within 0.5%.

The present inventors developed a non-invasive, highly portable, optoacoustic apparatus that rapidly assesses $SO_2$ in the innominate vein, which closely approximates $S_{svc}O_2$. The monitor transmits short-duration pulses of near-infrared (NIR) light, which are absorbed by oxygenated and deoxygenated Hgb and subsequently generate ultrasound signals that accurately measure $SO_2$. This novel optoacoustic technology could obviate the need for central venous catheterization, while accurately and frequently assessing central venous $SO_2$ for casualties in shock or at risk for shock.

Optoacoustic technology: Laser optoacoustic imaging techniques combine the merits of optical tomography (high optical contrast) and ultrasound imaging (insignificant scattering of acoustic waves) to yield a noninvasive diagnostic modality with high contrast, sensitivity, and resolution. The high resolution, sensitivity and contrast of optoacoustic techniques provide monitoring of total Hgb concentration, oxygenated Hgb, deoxygenated Hgb and, depending on the wavelengths used, carboxyHgb and metHgb with excellent accuracy, specificity and sensitivity. Laser optoacoustics, recently developed as a technique for tissue characterization and diagnostic imaging, provides continuous, noninvasive, highly accurate measurement. Optoacoustic techniques utilize sensitive detection of laser-induced ultrasonic waves rather than optical signals. Because the acoustic waves travel in a straight line from the source, the depth of the target blood vessel can be precisely calculated from the time required for the signal to return and the speed of sound through tissue. Transmission of ultrasound signals in a straight line differentiates optoacoustic measurements from pure optical measurements, in which returning optical signals are scattered, as is the incident light. Time-resolved detection of the pressure profiles by ultrasound transducers and analysis of the pressure signals facilitate high-resolution reconstruction of optoacoustic images. Optoacoustic techniques can pinpoint structures in optically turbid and opaque tissues at depths as great as eight centimeters with spatial resolution≤0.5 millimeters and to reconstruct optoacoustic images.

OxyHgb and de-oxyHgb have high absorption coefficients in the visible and NIR spectral range. Therefore, both the amplitude and spatial distribution of the generated optoacoustic pressure induced in blood are dependent on the Hgb saturation and concentration (calculated as oxyHgb÷total Hgb). High z-axial resolution of the optoacoustic technique permits direct measurement of Hgb saturation in large blood vessels because the optoacoustic waves induced in blood arrive at the acoustic transducer at a time that is directly proportional to the speed of sound in tissue. Since the Hgb absorption coefficient is dependent on Hgb $SO_2$, laser sources with wavelengths of approximately 805 nm (isosbestic point where oxyHgb and deoxyHgb have equal absorption) for are utilized for Hgb monitoring; and then, using the obtained [Hgb] value, wavelengths of approximately 1064 nm are used for oxygenation monitoring because oxyHgb and deoxyHgb have strong differences in absorption. Thus, by analyzing the temporal profile of optoacoustic pressure induced in blood by pulsed laser NIR light of various wavelengths, the absolute value of Hgb $SO_2$ can accurately be obtained.

In some embodiments, the emitted light is within the low end of the NIR spectral range, such as approximately 600 to 1300 nm, for example 760 nm, 800 nm, and 860 nm. Such a wavelength range can result in deep penetration of the NIR radiation, which is sufficient for optoacoustic monitoring of hemoglobin saturation. The amount of laser energy applied for monitoring may be small and cannot induce any thermal or mechanical damage to a patient's skin or a patient's or operator's ocular tissues because laser fluence levels are well below the maximum permissible exposures (MPE) for ocular tissues. In some embodiments, the laser energy is delivered at a power of approximately 1 µJ to 1 mJ.

Oxyhemoglobin and deoxyhemoglobin have high absorption coefficients in the visible and NIR spectral range. Therefore, both the amplitude and spatial distribution of the generated optoacoustic pressure induced in blood are generally dependent on total hemoglobin concentration [THb] and hemoglobin saturation (calculated as oxyhemoglobin/[THb]). The high resolution of the disclosed measurement technique enables direct measurement of [THb] and saturation in large blood vessels. In some embodiments, saturation can be assessed using an optical parametric oscillator (OPO) pumped by Nd-YAG laser to generate four important wavelengths: 800 or 805 nm (isosbestic point where oxy- and deoxyhemoglobin have equal absorption) and 700, 730, and 760 nm, which are wavelengths at which oxy- and deoxyhemoglobin have strong differences in absorption. In some embodiments, the concentration of different molecules may be of interest such that other wavelengths are chosen.

As previously mentioned, the acoustic signal generally returns in a straight line from the target. Laser optoacoustic imaging techniques combine the merits of optical tomography (high optical contrast) and ultrasound imaging (minimal scattering of acoustic waves) to yield a noninvasive diagnostic modality with high contrast, sensitivity, and resolution. The high resolution, sensitivity, and contrast of optoacoustic techniques provide monitoring of [THb], oxygenated and deoxygenated hemoglobin with excellent accuracy, specificity and sensitivity. Transmission of ultrasound signals in a straight line differentiates optoacoustic measurements from pure optical techniques in which both incident and returning optical signals are scattered by passage through tissue. Optoacoustic imaging can visualize structures in optically turbid and opaque tissues at depths as great as several centimeters with a spatial resolution ≤0.5 mm and can reconstruct optoacoustic images. In summary, the merits of optoacoustic monitoring include, but are not limited to: (1) noninvasiveness, (2) accurate, quantitative measurements, (3) continuous, real-time monitoring, (4) high spatial resolution, and (5) compact dimensions.

In clinical optoacoustic monitoring of $SO_2$ in the innominate vein, the acoustic detector will monitor signals that return toward the optical source (backward mode). Merits of optoacoustic monitoring include: 1) noninvasiveness, 2) accurate, quantitative measurements, 3) continuous, real-time monitoring, 4) high spatial resolution, 5) compact dimensions. In certain embodiments the system is miniaturized to operate from a device the size of or smaller than a notebook computer thus permitting wide application of the sensor at all echelons of care.

The following examples are include for the sake of completeness of disclosure and to illustrate the methods of making the compositions and composites of the present invention as well as to present certain characteristics of the compositions. In no way are these examples intended to limit the scope or teaching of this disclosure.

EXAMPLE 1

Comparative Studies of Venous $SO_2$ in the Basilic Vein (BV) and Internal Jugular Vein (IJV)

In vivo tests in large animals (sheep) demonstrated that a prototype system measures $SO_2$ accurately and precisely (correlation: $r^2$ 0.99; bias=2.47%; SD=±2.3%) in comparison to the gold standard hemoximetry. In a previous study, the present inventors built a dual-probe optoacoustic prototype that was designed to detect and compare venous $SO_2$ in the basilic vein (BV) and internal jugular vein (IJV) by both a validation study and a clinical concept testing. The validation study focused on the IJV oxygenation comparison between optoacoustic and the gold standard hemoximetry. See Petrov I Y, et al Optoacoustic measurement of central venous oxygenation for assessment of circulatory shock: clinical study in cardiac surgery patients. *Proc. SPIE* 8943 (89430Y) (2014) 1-5. In brief, the IJV was interrogated by ultrasound (U/S), depth was recorded, and the skin was marked for IJV borders. FIG. 1A shows an ultrasound image of the right internal jugular vein of a sheep. The optoacoustic probe was placed on the anterior neck surface and measured for optoacoustic oxygenation. FIG. 1B shows the optoacoustic signal obtained from the IJV at the 10-11 mm point shown in FIG. 1A. A central line was placed and confirmation hemoximetry from IJV was obtained using the finder needle. FIG. 1C shows optoacoustic determination of venous oxygen 82±2% versus 83% via co-oximetry [dashed line]. Data showed that the depth calculated by U/S and optoacoustics for IJV were ±1.7 mm and the venous oxygen saturation $SO_2$ measurements for comparing hemoximetry to optoacoustic were 3±2%, demonstrating high accuracy. Thus, comparing gold-standard measurements for IJV oxygenation and signal acquisition depth can accurately be obtained by the optoacoustic prototype.

The clinical concept testing focused on the optoacoustic determination of the venous oxygenation gradient (central [internal jugular oxygenation—$S_{IJV}O_2$] minus peripheral [basilica venous oxygenation gradient—$S_{BV}O_2$]) in induced hypovolemia. Specifically, the venous oxygenation gradient ($S_{IJV}O_2$–$S_{BV}O_2$) was determined to indicate appropriate physiologic compensation (decrease in $S_{IJV}O_2$–$S_{BV}O_2$) during progressive hypovolemia. In brief, volunteers (n=5) were placed in a lower body negative pressure (LBNP) chamber. LBNP was progressively induced until blood pressure (BP) fell (LBNP 60 mmHg).

Figure 2B:
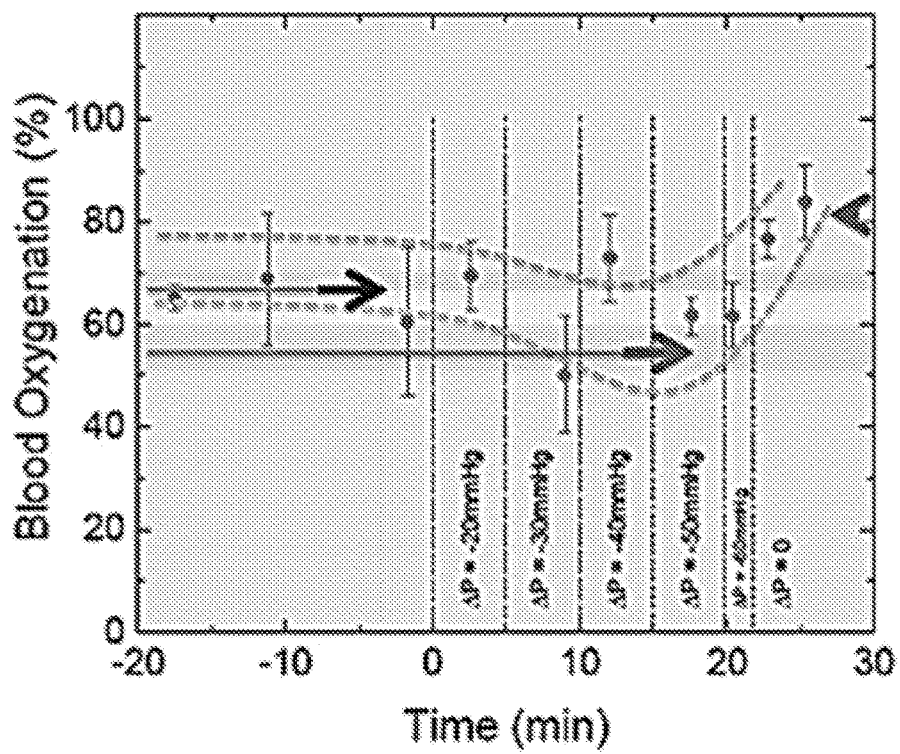
FIG. 2B shows determinations of blood oxygenation optoacoustically measured over the IJV during LBNP.
Figure 2C:
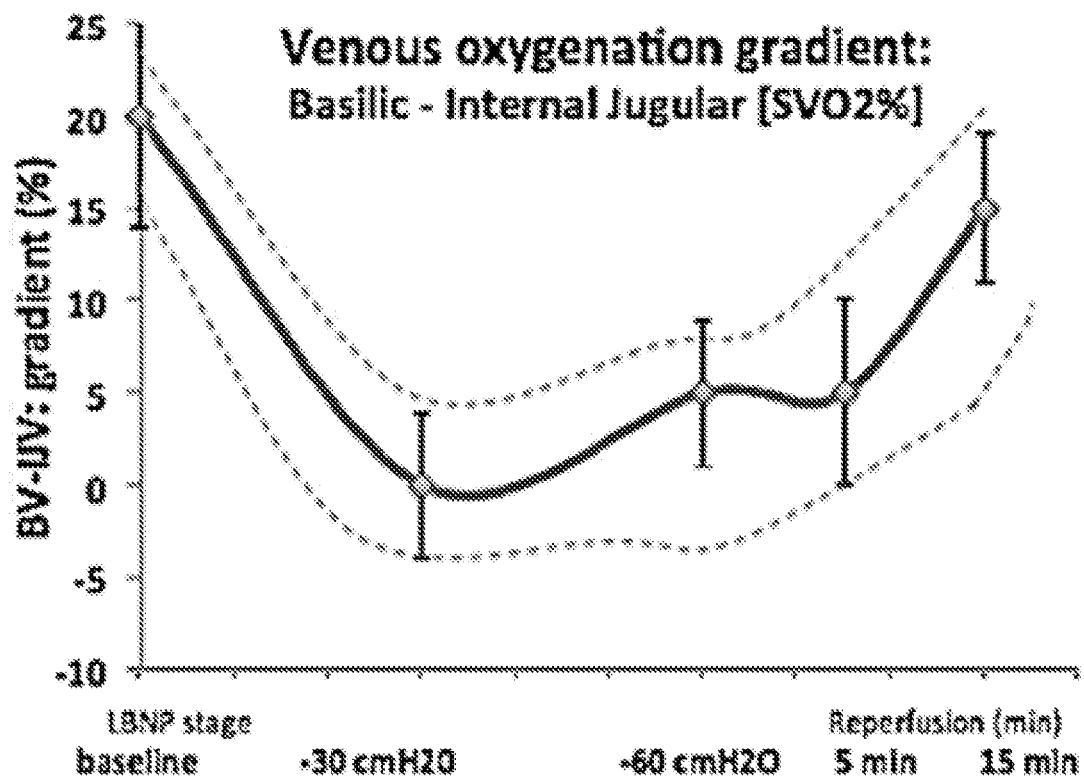
FIG. 2C shows the venous oxygenation gradient between the BV and the IJV during LBNP.

In the initial compensatory stage of shock, blood flow to the peripheral (skin, muscle, etc.) circulation is reduced in order to preserve vital organ (brain, heart) perfusion. Characteristically, this can be observed by a greater reduction in peripheral venous oxygenation (for instance, the basilic vein [BV]) compared to central venous oxygenation (the internal jugular vein [IJV]), which undergoes little change. While invasive measurements of oxygenation are accurate, they lack practicality and are not without complications. Our novel optoacoustic system noninvasively determines oxygenation in specific veins. To test this application, we placed two optoacoustic probes, guided by ultrasound imaging, over the BV and IJV and initiated the lower body negative pressure (LBNP) system. LBNP simulates hemorrhage by exerting suction on the lower body, thereby reducing the volume of blood available for central circulation. LBNP began at −20 mmHg, thereafter was reduced in a step-wise fashion (up to −60 mmHg). The optoacoustically measured BV oxygenation largely decreased with LBNP—FIG. 2A (top vs bottom arrow), whereas IJV oxygenation—FIG. 2B (top vs bottom arrow) underwent a more modest decrease. Restoration of normal blood flow occurs promptly upon cessation of LBNP (red vs green arrows). The resulting venous oxygenation gradient (FIG. 2C) decreased indicating appropriate physiologic compensation to hypovolemia. These results indicate that the optoacoustic system may provide safe and rapid measurement of peripheral and central venous oxygenation and diagnosis of shock with high specificity and sensitivity.

Although the dual-probe optoacoustic based system detected differences between the two venous sites and could confirm the development and resolution of shock, there were significant limitations, including: signal instability, movement artifacts, difficult characterization of the oxygenation gradients (basal versus reperfusion state), and inability to measure $SO_2$ in the basilic vein ($SbvO_2$) due to vein collapse during LBNP-induced hypovolemia. These challenges have led us to re-examine our design and develop a different and robust approach.

EXAMPLE 2

Initial Development of $S_{LIV}O_2$ Measurement

Figure 3A:
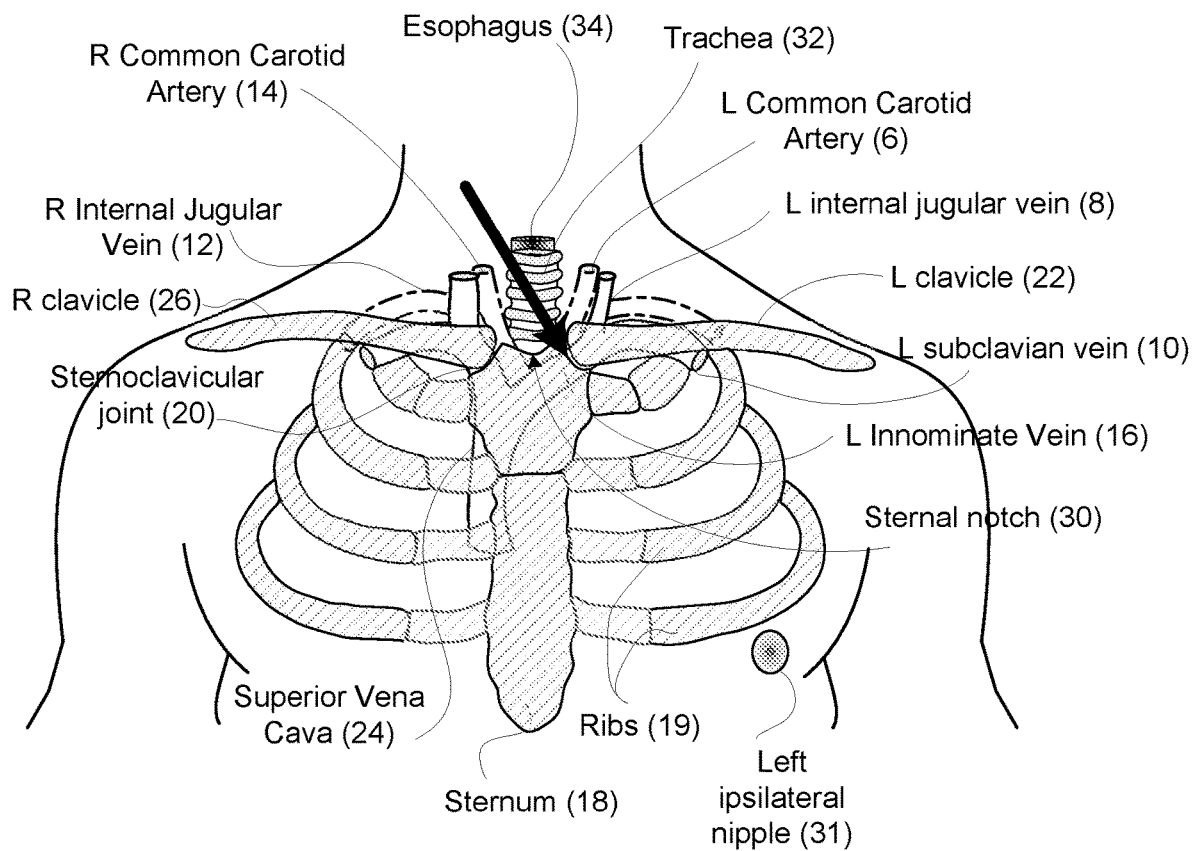
FIG. 3A and FIG. 3B show certain aspects of the venous, arterial and skeletal anatomy of the upper thorax.
Figure 3B:
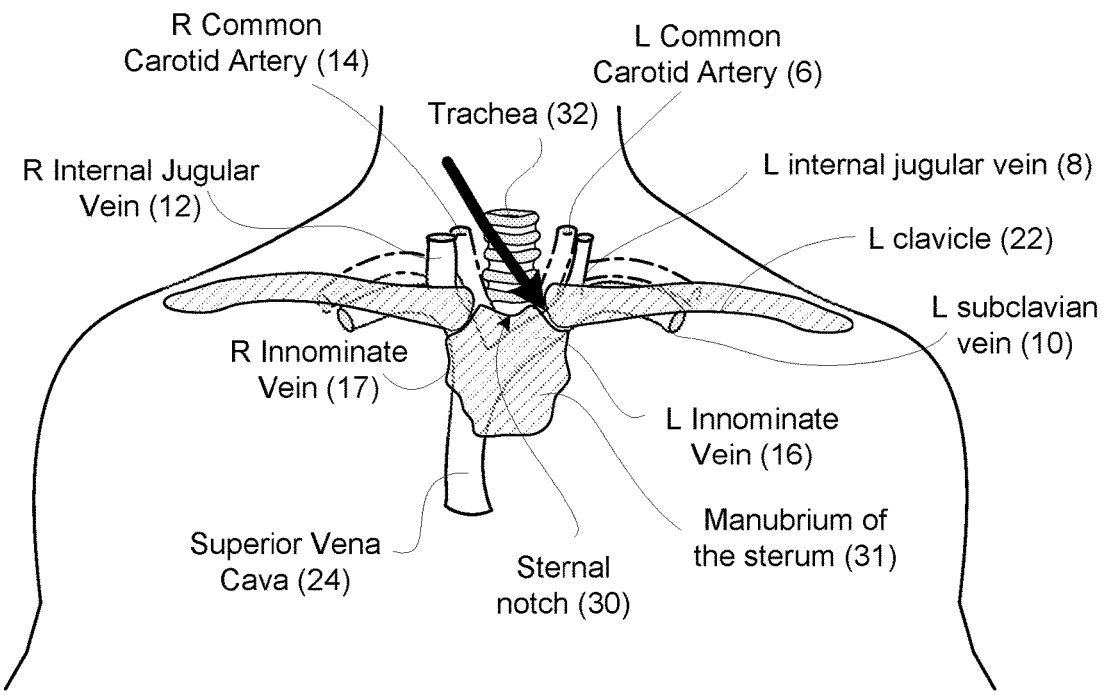

In efforts to improve $SO_2$ measurements for identifying and monitoring shock, several important improvements were made. First, signal stability was achieved through use of a laser diode-based optoacoustic system with a high pulse repetition rate. This facilitated rapid measurements in real-time. Next we identified an ultrasound and optoacoustic window that allowed us to interrogate the left innominate vein (LIV) through the supra-sternal notch. Certain of the venous, arterial and skeletal anatomy of the upper thorax is shown in FIG. 3A and FIG. 3B which show the left clavicle (22) and the right clavicle (26) and the connecting central, upper manubrium (31) of the sternum (18) also showing attachment of the upper ribs (19) to sternum (18). At the top center of the manubrium lies the suprasternal (aka sternal) notch (30), which overlies the left innominate vein ("LIV") (16) and the right innominate vein ("RIV") (17) and their connection to the superior vena cava ("SVC")(24). The placement of manubrium (31) in relation to the trachea (32) is shown in FIG. 3B, which eliminates certain features of FIG. 3A in order to more clearly depict the location of LIV (16) in relation to suprasternal notch (30). The heavy arrow shows the acoustic window for LIV (16), which is lateral and to the left of the suprasternal notch at a depth of 1-3 cm.

Anatomically, LIV (16) forms behind the left clavicle (22) and drains the left internal jugular vein ("IJV") (8) and the left subclavian vein (10). The LIV is easier to access than RIV (17), which is more fully behind sternum (18). Both LIV (16) and MV (17) drain into SVC (24). Thus, the LIV approximates central venous oxygenation ($S_{CV}O_2$), which has shown to be a superior endpoint in resuscitation from shock. Confirmation of whether the LIV oxygenation ($S_{LIV}O_2$) obtained by invasive catheterization is comparable to $S_{CV}O_2$ in a broad population of patients as well as mixed venous oxygen saturation by invasive pulmonary artery catheterization ($S_{PA}O_2$=mixed venous saturation=$S_VO_2$) will be obtained from clinical studies.

In one embodiment, an optoacoustic oxygenation monitoring system is provided to improve methods for resuscitation. Guiding resuscitative efforts based on $S_{LIV}O_2$ will better stabilize casualties with shock and TBI and provide an early detection of life-threatening injuries. Complimentary measures of brain venous oxygenation, such as $S_{IJV}O_2$ or $S_{SSS}O_2$, could help mitigate progressive brain injury. In one embodiment, $SO_2$ indices are incorporated into a decision support or autonomous platform that would include resuscitation limits, need for blood or other vasoactives. $S_{LIV}O_2$ does not suffer limitations by current perfusion assessment in field such as capnometry. Specifically, $S_{LIV}O_2$ does not require intubation and accuracy is not limited by anatomic and physiologic deadspace.

Figure 4A:
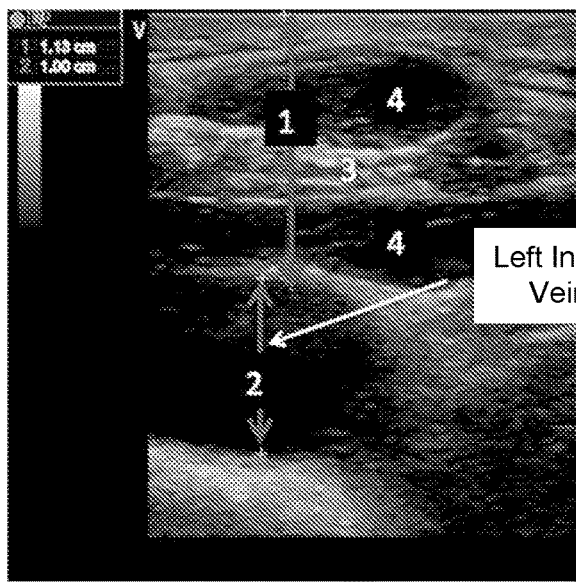
FIG. 4A and FIG. 4B show U/S measurements were made with a human subject supine with the head turned toward the left. To obtain the image in FIG. 4A, a 13 MHz ultrasound (U/S) probe (GE Vivide) was placed in the lateral to left supra sternal notch.
Figure 4B:
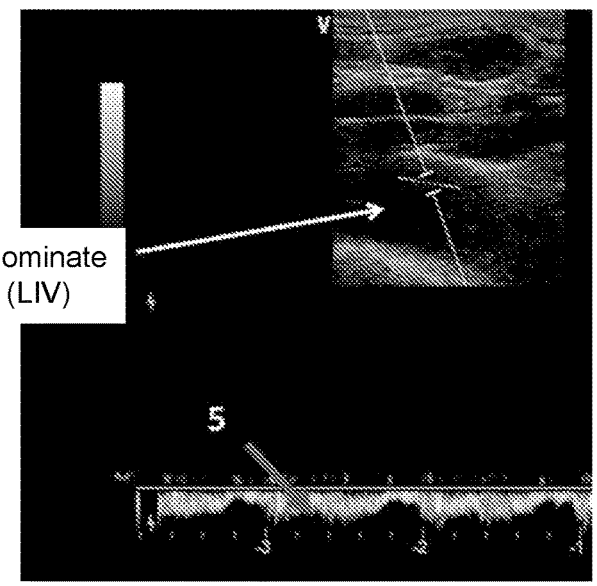

Optoacoustic determination of LIV access: Volunteers (n=5) were recruited to determine if an acoustic window for ultrasound and optoacoustic signals can be obtained for the innominate veins and in particular the LIV. Demographics of the volunteers were broad including: ages 24-70 yr, Ht. 160-195 cm, Wt. 50-119 kg and gender (4 males and 1 female). 2D and Doppler ultrasound ("U/S") were used to characterize the LIV in relation to the sternal notch. In brief, U/S (FIGS. 4A and 4B) and optoacoustic (FIG. 4C) measurements were made with the subject supine with the head turned toward the left. An acoustic U/S window for LIV was found 1-3 cm lateral to the left suprasternal notch with a 12 MHz probe (12L, General Electric, Milwaukee, WI) tilted 120-150° from skin surface and aimed towards the ipsolateral nipple. LIV was confirmed by 2D ultrasound (FIG. 4A) and Doppler waveform (FIG. 4B), both showing the LIV. To obtain the image in FIG. 4A, a 12 MHz ultrasound (U/S) probe (GE ultrasound imaging probe i12L-RS connected to a GE Vivide system) was placed in the lateral to left suprasternal notch. 2D image acquisition shows the left innominate vein (LIV) indicated by white arrow. The depth from skin surface to LIV (arrow 1) was 11.3 mm. LIV had a diameter of 10 mm (arrow 2). Connective tissue (3) and small muscle bands (4) also observed. FIG. 4B shows Pulse wave Doppler, positioned on center of LIV and demonstrates a low frequency venous pulse waveform (5) that varied with respiration.

Figure 4C:
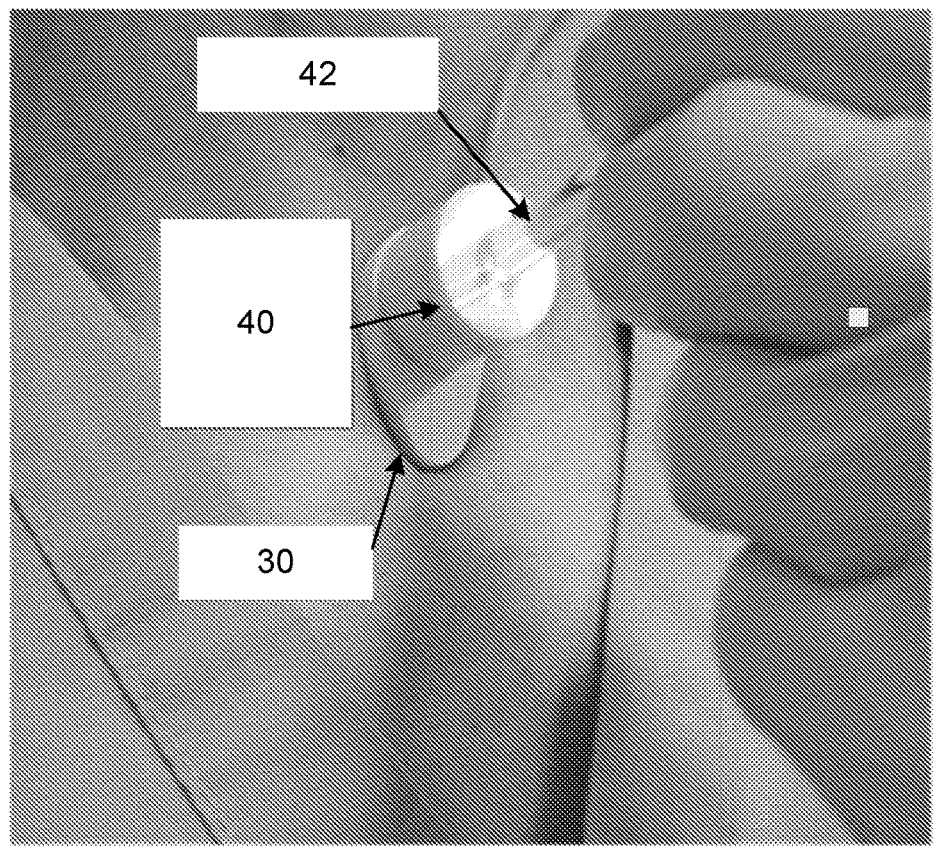
FIG. 4C shows placement of an optoacoustic detector over the sternal notch on a human patient.

The depth of the LIV by U/S [mean±SEM] was 10.3±0.8 mm. As depicted in FIG. 4C, after locating the LIV by ultrasound, an optoacoustic prototype probe was placed in a similar direction and plane. The probe housing 40, includes an internal optical fiber and acoustic transducer element, had a similar profile as the ultrasound probe including a flat, high surface area contact with skin. Probe housing 40 was easily maintained in a stable position on the patient by virtue of positional handle 42 affixed to housing 40.

Figure 5A:
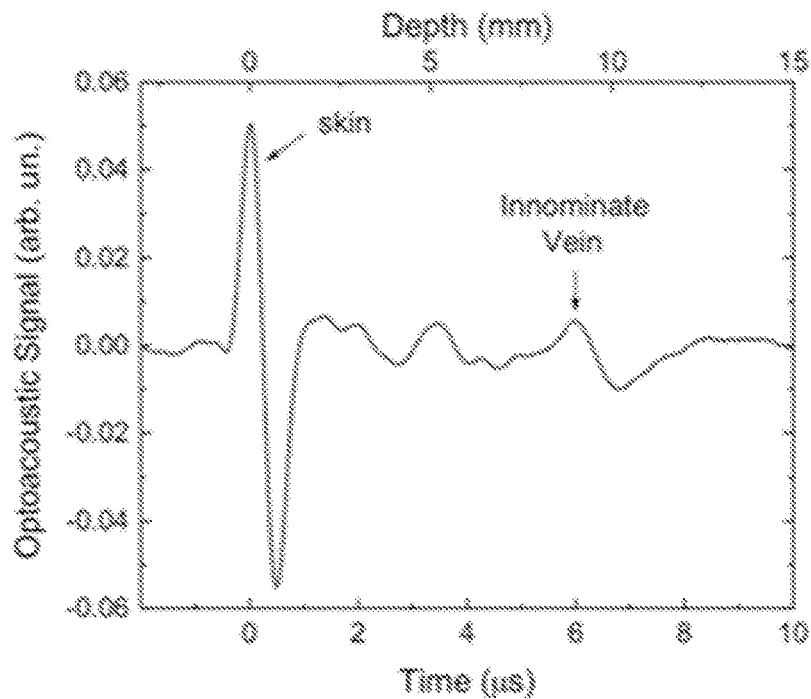
FIG. 5A shows optoacoustic signals for the LIV obtained with the prototype probe of FIG. 4C.

Oxygenation measurements of the LIV using optoacoustic prototype were confirmed by peak chromophore absorption signal at a depth consistent with ultrasound (9-10 mm below skin) (FIG. 5A). Once the absorption signal was obtained, $S_{LIV}O_2$ was determined from averaging 20-30 optoacoustic signals over 3-4 min (FIG. 5B) representative venous oxygenation from left innominate vein. Optoacoustic signal identification in FIG. 5A includes, skin, soft tissue [next peak] and innominate (LIV) based peak chromophore signal for LIV and depth.

Table 1 shows the range of $S_{LIV}O_2$ obtained in the 5 subjects. The mean±SEM for these subjects was 75±3%, which is similar to values in health for central venous oxygen saturation.

TABLE 1

Optoacoustic ("OA") vs Ultrasound U/S Depth and Oxygenation Determination in 5 Subjects

| Subject # | Depth: U/S (mm) | Depth: OA (mm) | $<S_{LIV}O_{2>}$, % |
|---|---|---|---|
| CSIV101 | 11.3 | 9 | 73.6 |
| CSIV102 | 10.3 | 11.4 | 73.7 |
| CSIV103 | 11 | 8.7 | 82.7 |
| CSIV104 | 11.8 | 9.3 | 75.3 |
| CSIV105 | 7.2 | 6 | 71.3 |

Figure 9A:
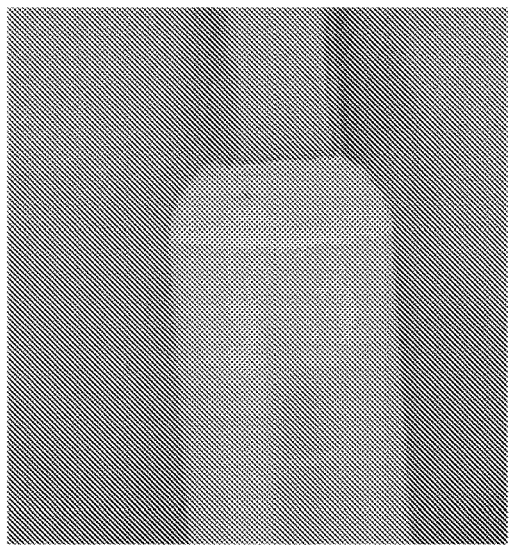
FIG. 9A and FIG. 9B show a new optoacoustic interface prototype. Specifically, the probe's face was elongated and narrowed to facilitate a more direct acoustic window as compared with the prototype of FIG. 4C.
Figure 9B:
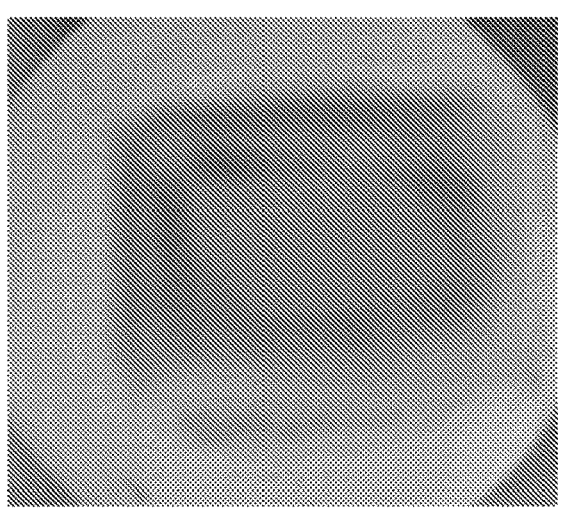

Of note, the depth measurements for optoacoustics ("OA") were slightly lower (8.9±0.8 mm) in most cases compared to U/S (10.3±0.2 mm) due to the small amount of skin displacement that is needed for the optoacoustic to skin coupling. While oxygenation data from the LIV could be obtained, the signal acquisition had some degree of variability. This was likely due to the optoacoustic probe's wide profile, rendering signal acquisition below the bend of the clavicle difficult. To address this issue, a new interface was prototyped as shown in FIGS. 9A and 9B. Specifically, the probe's face was elongated and narrowed to facilitate a more direct acoustic window as compared with the prototype of FIG. 4C. The design change allowed enhanced LIV interrogation. Additionally, since the LIV and probe alignment was improved, signal stability was augmented.

Figure 5B:
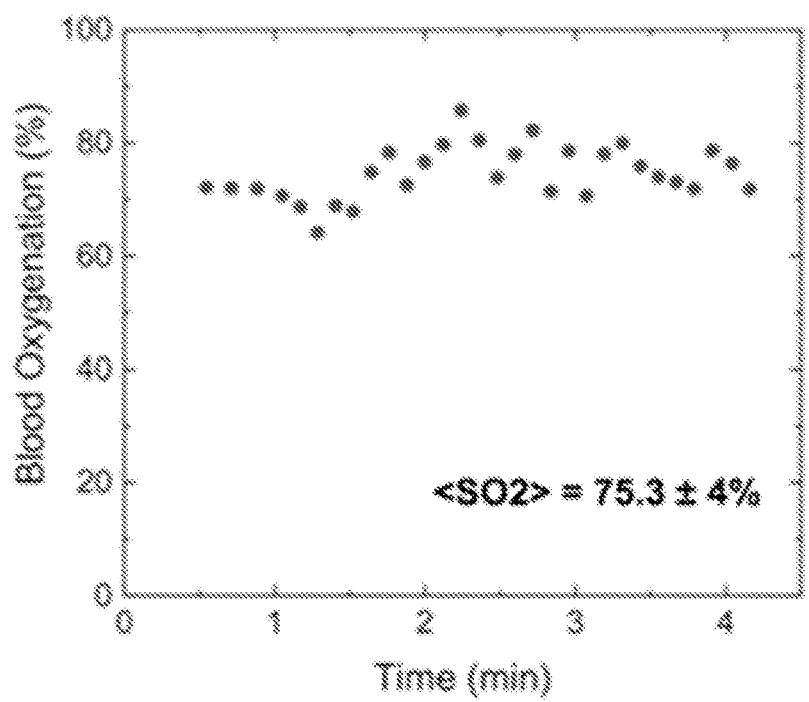
FIG. 5B shows the $S_{LIV}O_2$ determined from averaging 20-30 optoacoustic signals over 3-4 min.
Figure 6A:
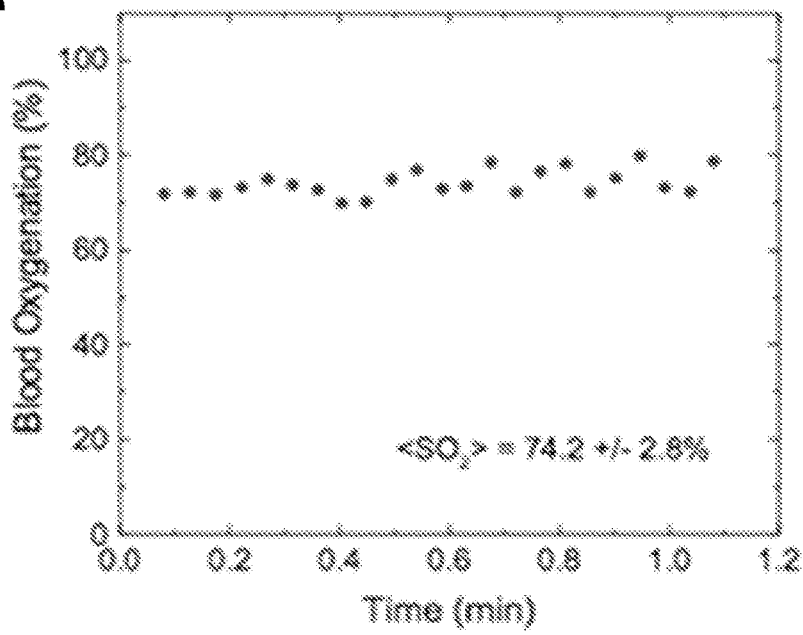
FIG. 6A and FIG. 6B show optoacoustic determination of venous oxygenation in same subject as FIGS. 5A-5B but with a design allowing a closer approach under the clavicle.
Figure 6B:
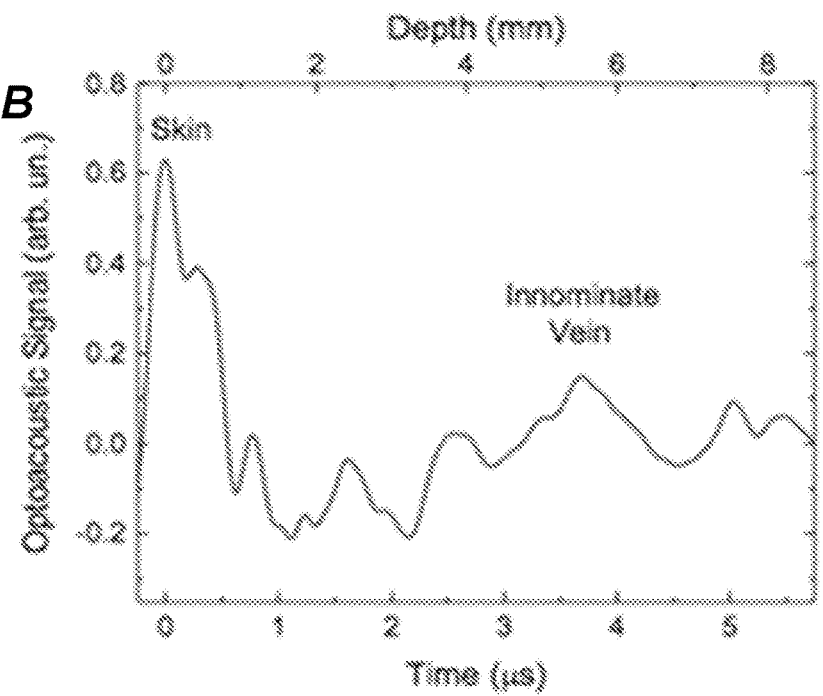
Figure 7A:
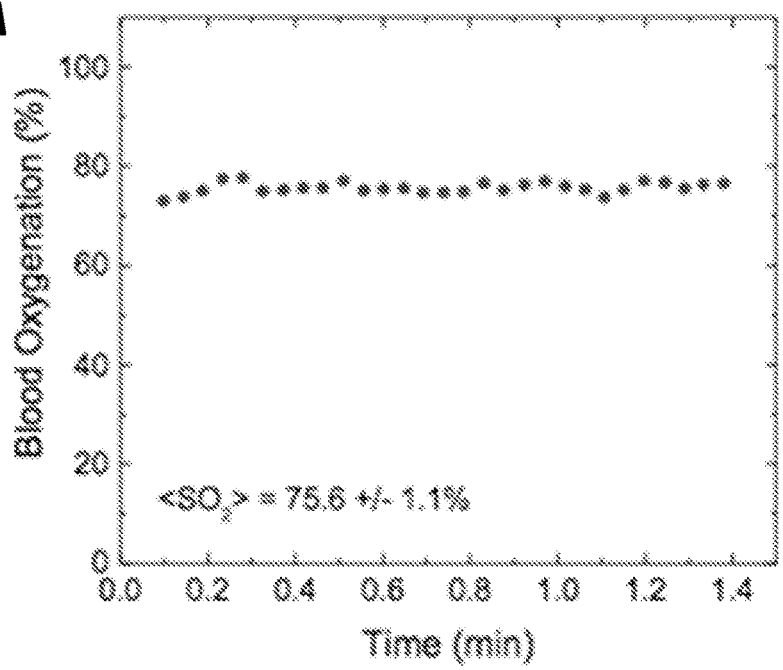
FIG. 7A and FIG. 7B show optoacoustic determination of venous oxygenation in same subject as FIGS. 5A-5B and FIGS. 6A-6B but with a design allowing a closer approach under the clavicle as used in generating the data of FIGS. 6A-6B.
Figure 7B:
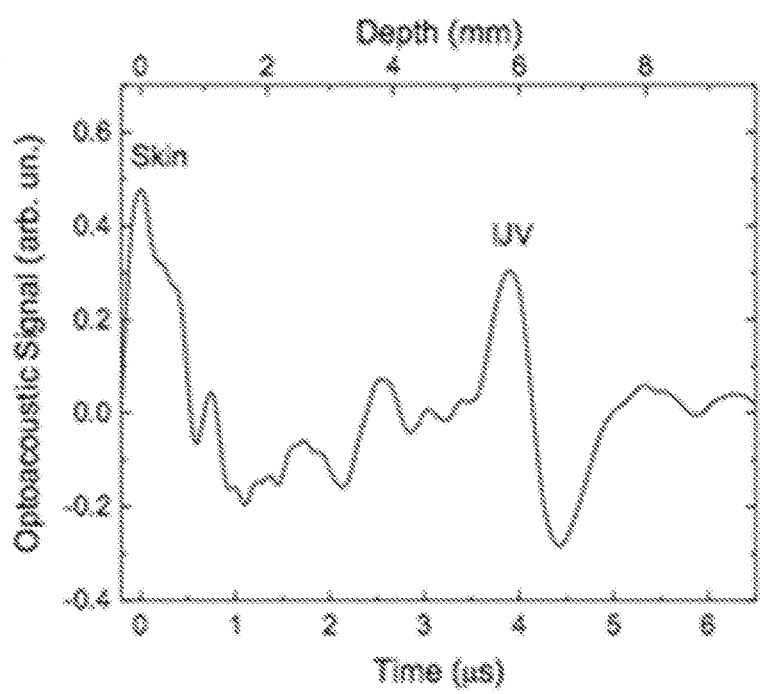
Figure 8A:
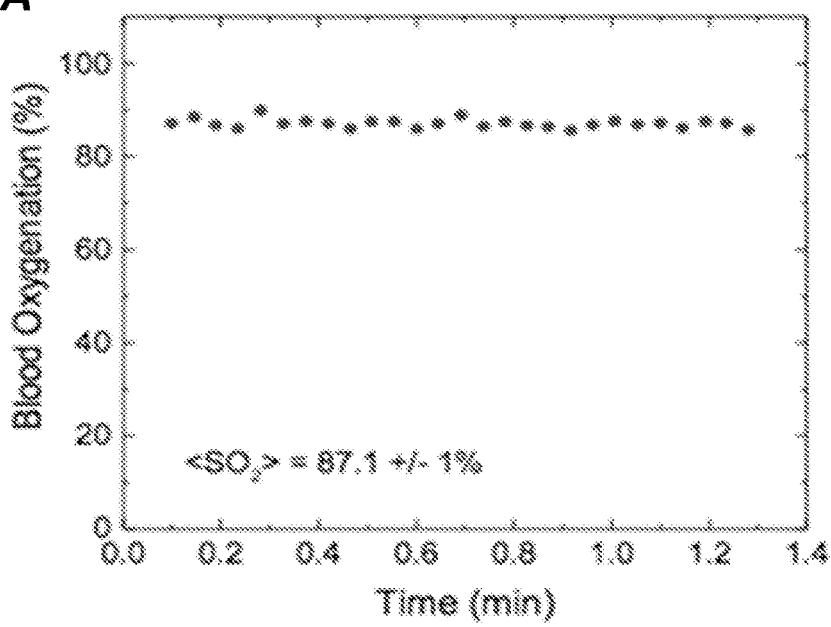
FIG. 8A and FIG. 8B show optoacoustic determination of venous oxygenation in same subject as FIGS. 5A-5B, FIGS. 6A-6B, and FIGS. 7A-7B but with a design allowing a closer approach under the clavicle as used in generating the data of FIGS. 6A-6B and FIGS. 7A-7B.
Figure 8B:
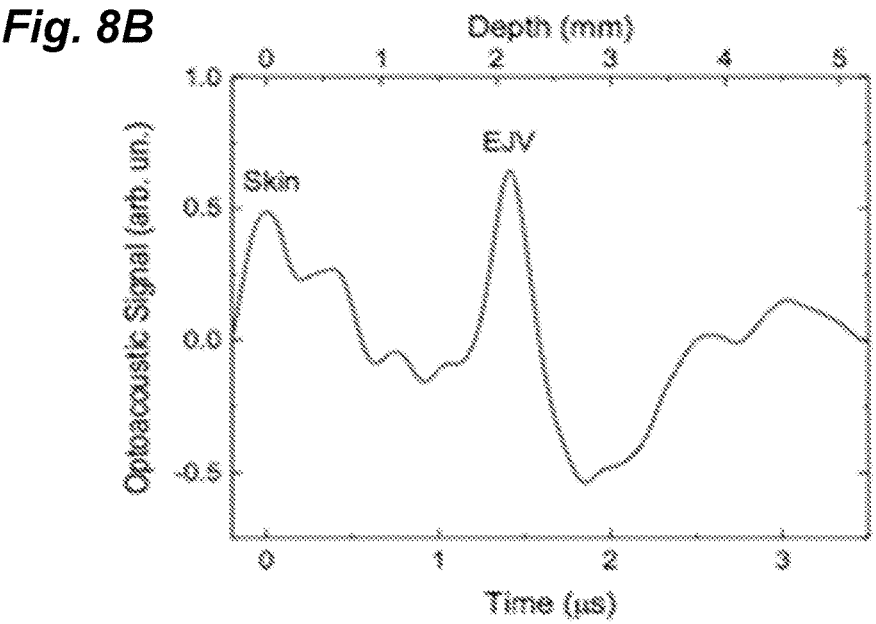

Using this design, optoacoustic oxygen saturation from left innominate vein (LIV), internal jugular vein (IJV) and external jugular vein, were determined in the same volunteer as the data depicted in FIGS. 5A and 5B. The probe interface allowed for greater contact with the skin surface. When the probe was placed under the clavicle and directed in a downward plane towards the left ipsolateral nipple (31) in FIG. 3A, a substantially greater tissue displacement (5-7 mm) was observed compared to previous measurements using the flatter probe (average of 2 mm: Table 1). The amount of displacement was confirmed firstly by measuring the coverage from the tip of probe to the exposed portion of the probe from the overlying clavicle surface skin. Secondly, the distance using 2D ultrasound from the skin surface to the left innominate vein was measured and subtracted from the optoacoustic derived peak signal from the LIV. As indicated, the depth determined by ultrasound and optoacoustics differ considerably with this new probe design. It was observed that the greatest difference was with optoacoustic innominate vein measurement for the new probe designed to fit under the clavicle. Additionally, the innominate vein is not a compressible structure from external tissue displacement. On the other hand, excess displacement of the probe over the IJV results in compression and loss of venous signal. Therefore, there is a limit on the amount of force that can be applied over the IJV. It should be noted that despite several mm of tissue displacement by the probe, it does not produce patient discomfort. Thus, optoacoustic innominate vein depth and $SO_2$ determination with this probe design will likely result in a closer signal from skin surface than the IJV in post patients. Having the peak chromophore signal closer to transducer confers the advantage of less scattering and greater signal stability, which likely explains the reduced signal variability. FIGS. 6A-6B, 7A-7B and 8A-8B show optoacoustic determination of venous oxygenation in same subject as FIGS. 5A and 5B. FIGS. 6A-6B show data for the left innominate vein with FIG. 6A showing blood oxygenation values and FIG. 6B showing the optoacoustic signal with depth through the tissue. FIGS. 7A-7B show data for the internal jugular vein with FIG. 7A showing blood oxygenation values and FIG. 7B showing the optoacoustic signal with depth through the tissue. FIGS. 8A-8B show data for the external jugular vein with FIG. 8A showing blood oxygenation values and FIG. 8B showing the optoacoustic signal with depth through the tissue. Oxygenation signal stability shows marked improvement.

The preliminary data demonstrate that venous $SO_2$, from a variety of venous sources, can be obtained using noninvasive, real-time, optoacoustic monitoring. Optoacoustic determination of venous oxygenation over the LIV, which lies beneath the left clavicular head, is an innovative approach to rapidly and non-invasively assess central venous oxygen saturation. The same technology platform can also be used to determine brain oxygenation including for initial TBI assessment and for monitoring brain oxygenation during Prolonged Field Care ("PFC"). We have measured oxygenation in the venous effluents for internal jugular vein ($S_{IJV}O_2$) and superior sagittal sinus ($S_{SSS}O_2$).

EXAMPLE 3

Noninvasive Optoacoustic Measurement of $S_{LIV}O_2$ to Permit Rapid Recognition of Shock In one embodiment methods and apparatus are provided for noninvasive optoacoustic measurement of $S_{LIV}O_2$ to permit rapid recognition of shock and to subsequently provide robust resuscitation monitoring so that under and over-resuscitation do not occur. In certain cases, noninvasive monitoring of $S_{LIV}O_2$ is complemented by determining brain oxygenation with $S_{IJV}O_2$ or superior sagittal sinus ($SsssO_2$) for TBI assessment. Optoacoustic determination of venous oxygenation can also be used as an adjunct monitor to prevent excessive PEEP, need for blood transfusion and other seamless adaptations for prolonged field care that includes: optimizing PEEP [$SpO_2$ vs $S_{LIV}O_2$], vital fluid choices [need for blood transfusion vs other fluids] and reducing oxygen consumption needs [fever, shivering thermogenesis vs need for paralysis fluid and sedation and anesthesia].

In one embodiment, a clinical validation protocol is used to establish efficacy of a device and method for ultrasound guided optoacoustic monitoring of oxygen saturation. In one such embodiments, cardiac surgical patients are tested by comparing hemoximeter-derived oxygen saturation to noninvasive optoacoustic saturation. A pulmonary artery (PA) catheter is placed via left internal jugular introducer sheath. Each patient receives a series of optoacoustic and hemoximetry measurements. In one embodiments, validation is obtained that that LIV is equivalent to SVC oxygenation in a large population of patients: Blood samples from an introducer inserted through the left internal jugular vein into the LIV is compared to proximal port (SVC) samples. In certain embodiments, physiologic validation is be obtained by comparing optoacoustic $S_{LIV}O_2$ to hemoximetry LIV in cardiac patients during different physiologic states e.g., pre-surgery, three ICU time points and discharge.

In certain embodiments, physiologic validation of optoacoustic $S_{LIV}O_2$ versus hemoximetry LIV is conducted. For each patient, data is collected including the type of surgery, duration of surgery and duration of pump run. Concurrent diseases and treatments may also be recorded, including blood, fluid and inotrope/vasopressor infusion. In addition, demographic data is collected including gender, age, ethnicity, ejection fraction and other cardiac abnormalities. Sub-analyses is then be performed using logistic regression to determine if any of these factors influence the optoacoustic measurements. Comparisons will be made from cardiac patients during different physiologic states that occur during the perioperative period e.g., pre-surgery, OR post-surgery and three ICU time points.

Figure 10:
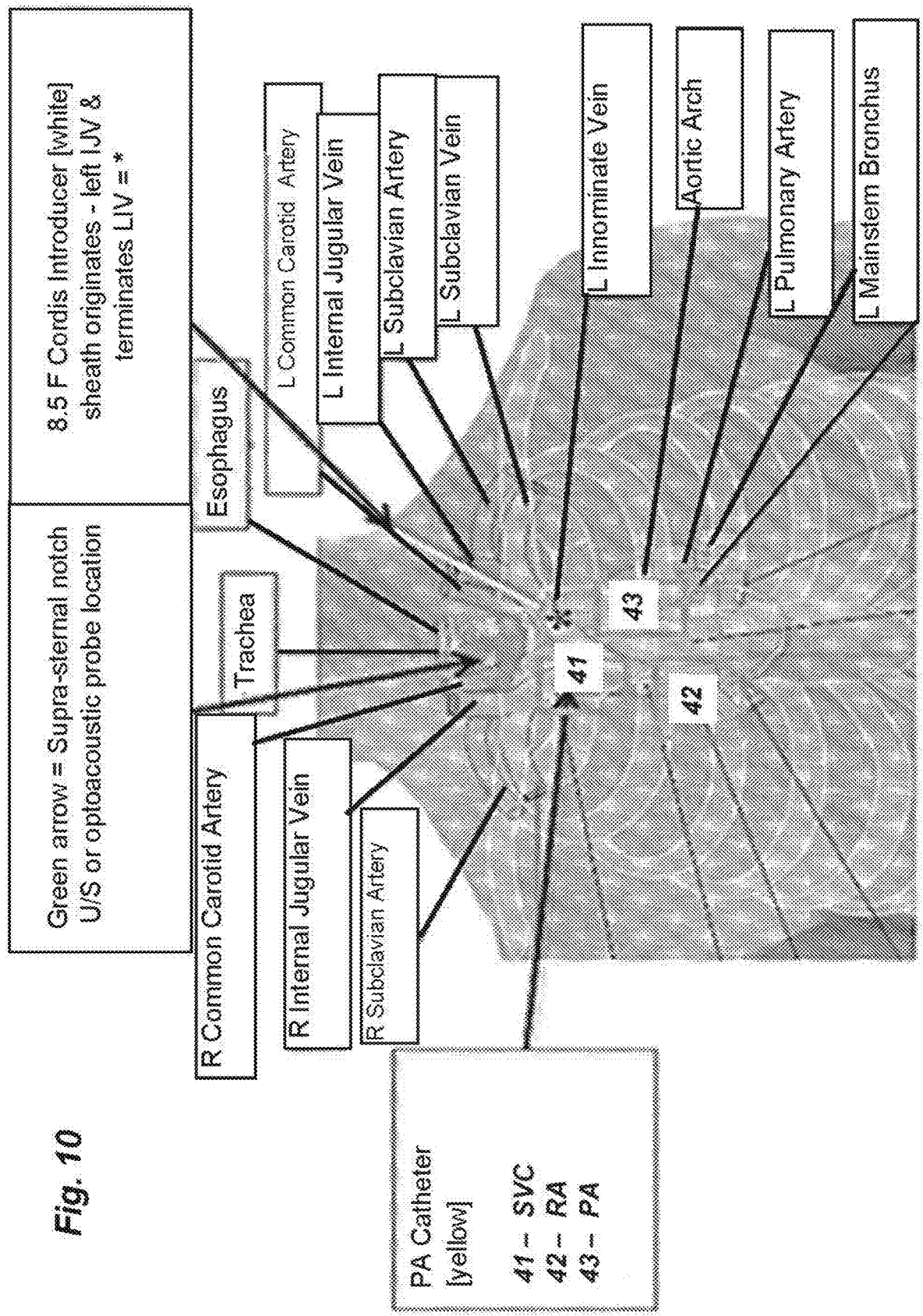
FIG. 10 depicts one protocol for sampling to confirm that sampling the left innominate vein (LIV) will correlate strongly with concurrent superior vena cava (SVC) oxygen saturation over an operative and perioperative course.

Validation of venous oxygenation equivalence is undertaken in certain embodiments. Pulmonary artery catheterization and monitoring are the standard of care for cardiac surgery. In one embodiment, equivalence testing could include placement of an introducer sheath (such as for example an 8.5 French Cordis or similar introducer sheath) into the left internal jugular by the anesthesiologist in an operating room under general anesthesia or sedation. A pulmonary artery ("PA") catheter (such as for example an Edwards LifeScience PA catheter or the like) is then placed with the tip of the catheter located in the pulmonary artery and confirmed by PA occlusive waveform. One approach for comparing oxygenation measurements is shown in FIG. 10. The PA catheter has three ports that include the infusion port (super vena cava), proximal port (right atrium) and distal port (pulmonary artery).

Finally, in one embodiment, optoacoustic determination of $S_{LIV}O_2$ using healthy volunteers includes induction of lower body negative pressure (LBNP) to simulate hypovolemic shock. Each volunteer undergoes progressive LBNP until pre-syncope or hypotension develops. Optoacoustically measured $S_{LIV}O_2$ is compared to SVC blood, obtained from an oximetric PA catheter infusion port, at each LBNP stage to demonstrate the feasibility and accuracy of noninvasive monitoring of LIV saturation. $S_{IJV}O_2$ may also be optoacoustically measured during each LBNP stage as a surrogate for brain oxygenation.

Figure 9C:
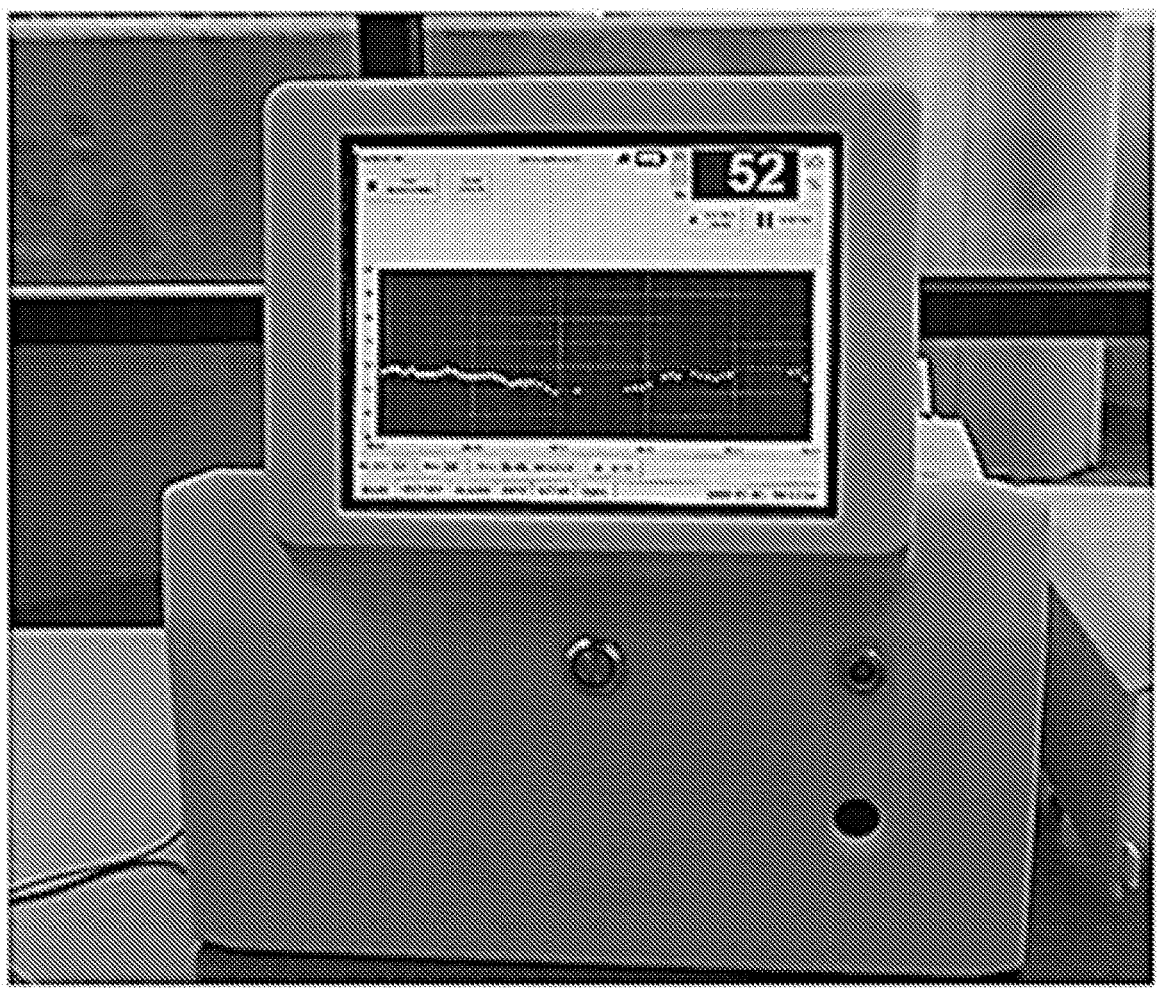
FIG. 9C shows an embodiment of an optoacoustic system with data display.

Initially in our studies, three consoles were designed and built that contained an optical rametric oscillator (OPO) as a laser source; a touch-screen, medical grade computer; power supplies and other control equipment. A fourth prototype system was built for measuring brain saturation in patients with TBI. FIG. 9C depicts one such prototype of a display for an optoacoustic monitoring system initially designed for monitoring sagittal sinus saturation through the intact skull in patients with TBI. This system can be markedly reduced in size for interrogating the left innominate or internal jugular veins since small laser power is only required to penetrate soft tissue. In one embodiment a system for prolonged field care could weigh less than or equal to 2.0 kg.

This prototype used pulsed laser diodes (PLD) stacks that have a higher repetition rate (1000 Hz) but utilize essentially the same control software and connecting cables. The higher pulse repetition frequency substantially reduces motion artifact vulnerability. Further, the PLD prototype has a smaller footprint and is therefore portable. In certain embodiments the diode-based system is miniaturized to a fraction of its current size, estimated to be ~2.0 kg, because much less power is required to penetrate a few cm of soft tissue above venous structures. Our In vitro testing shows that a measurement of venous saturation can be completed within 30 seconds and the system can continuously update measurements every 1-3 seconds using a PLD system. In certain embodiments, the system provides for acquisition of more signals per second therefore reduce scanning time.

There are specific peak signals that are associated with depth, vessel size and chromophore characteristics. In certain embodiments, a novel peak signal recognition program may be employed that automatically identifies signals originating in clinically relevant veins, including the IJV, LIV, EJV, SCV, femoral (FV) and BV veins. This is similar to machine learning. The automated software can choose the largest signal from the detector when best positioned and convert those signals into quantitative saturation data. Software that digitizes and filters out background signals can also be used to enhance signal architecture. For example, when the probe is placed over the suprasternal notch and aimed left towards the left nipple various tissues are present e.g., connective tissue, small muscle bands and LIV. On the other hand, when pointing toward the right nipple, which has similar tissues but is over the right innominate vein, since it is in a deeper field, the homologous location can be used to subtract out or filter these signals.

In certain embodiments, further clinical validation protocols are used to establish efficacy of a device and method for ultrasound guided optoacoustic monitoring of oxygen saturation. Studies on volunteers generates requisite anatomic and trajectory data that define the anatomy of the acoustic window over the target vein including one or more of the IJV, LIV, EJV, SCV, femoral (FV) and BV veins.

In one embodiment of a clinical validation protocol used to establish efficacy of a device and method for ultrasound guided optoacoustic monitoring of oxygen saturation, the LIV is targeted and the optoacoustic trajectory for optimizing oxygenation signals is obtained. In one embodiment, volunteers are placed in supine in a trendelenburg position. For each subject, measurements are made via ultrasound: distance from skin surface to vessel surface and midpoint, innominate vessel diameter, velocity profile by pulse wave Doppler and color flow mapping. An ultrasound probe is placed in the suprasternal notch and aimed at the left ipsilateral nipple until the innominate vein is found. The angle and direction of the ultrasound probe in relation the body in two different axis, at which the innominate vein is best interrogated, will be measured using an adjustable protractor arm. The two axis include: caudad to cephalad and medial to lateral. After the ultrasound measurements are complete, the optoacoustic probe is used to measure innominate vein oxygen saturation. In certain embodiments an iterative probe interface is used. An ultrasound probe is first applied to the patient and the vessel of interest is located. The interface is left in place stably affixed to the patient and the optoacoustic probe is placed in the interface. In certain embodiments, a force transducer is attached to a surface of the optoacoustic probe in order to measure the amount of force (tissue displacement) required in order to obtain the peak and optimal signal from a light source such as a pulsed laser diode ("PLD"). Optoacoustic measurements e.g., depth of vessel and oxygenation calculations will be continuously recorded after peak signal is obtained. All measurements are non-invasive.

Pulmonary artery catheterization and monitoring are standard of care for cardiac surgery. After obtaining written informed consent from patients, an introducer sheath (such as for example, an 8.5 French Cordis sheath or the like) is placed into the left internal jugular in the OR under general anesthesia or sedation. The PA catheter (such as for example an Edwards LifeScience PA catheter or the like) is placed with the tip of the catheter located in the pulmonary artery and confirmed by PA occlusive waveform. This approach for comparing oxygenation measurements is shown in FIG. 10. The PA catheter has three ports that include the infusion port (super vena cava), proximal port (right atrium) and distal port (pulmonary artery). Referring to FIG. 10, showing the addition of a white Cordis introducer sheath that terminates with a port in the LIV (indicated by *). The PA catheter has three ports; the infusion port—located in the superior vena cava (SVC), as indicated by 41, proximal port—located in right atrium (RA) as indicated by 42 and distal port—located in the PA as indicated by 43.

The introducer sheath (which is 15 cm in length in the case of a Cordis catheter), has one port. Based on the length and placement, this nearly guarantees that the tip of the introducer sheath catheter will located in the innominate vein. Once the catheters are secured, ultrasound is used to confirm that the tip is located in the LIV. Ultrasound measurements may also determine the depth of the LIV from surface of skin. Determination of the distance, in mm, from the introducer sheath tip to genu of the left IJV may be made. In order to compare venous oxygenation from different sites, blood is sampled from the introducer in the LIV, SVC and PA (representing mixed venous) and sent for hemoximetry (such as for example using an IL 682 Co-Oximeter, Instrument Laboratories, Bedford MA). In certain embodiments, venous blood samples are performed at distinct time points or periods for each subject. For example, specific time points may include: 1) baseline, which is defined after catheter placement but before surgery, 2) at end of surgery but prior to ICU transport, 3) one hour after ICU arrival, 4) post-operative day 1 in ICU before extubation, and 5) post-operative day 1 in ICU after extubation and immediately prior to removing the PA catheter. Data analysis is conducted to confirm that sampling the left innominate vein (LIV) correlates strongly with concurrent superior vena cava (SVC) oxygen saturation over perioperative course in a wide population sample. Data will be compared by linear regression with $S_{LIV}O_2$ (hemoximetry) plotted on the Y-axis versus in $S_{SVC}O_2$ on the X-axis.

In one embodiment, in the same subjects outlined above, hemoximetry samples from the introducer port are compared to innominate vein saturation [$S_{LIV}O_2$] measured optoacoustically. The optoacoustic probe is placed in the suprasternal notch and directed towards the left innominate vein as previously described. Optoacoustic signal acquisition is done for 2-3 minutes to ensure adequate sampling time. For each optoacoustic measurement, the mean and standard deviation are performed. Each subject will undergo comparative measurements for optoacoustics and hemoximetry at the time points outlined previously. Blood from PA site will also be compared as this represents mixed venous blood.

$S_{LIV}O_2$ measured by optoacoustics is compared to determine strong correlation with simultaneous measurements of $LIVO_2$ saturation measured via hemoximetry. For example, data may be compared by linear regression, in which optoacoustic $S_{LIV}O_2$ are plotted on the Y-axis versus hemoximetry $LIVO_2$ saturation on the X-axis. In certain embodiments, measurements are compared using the Bland-Altman approach, in which the difference between $S_{LIV}O_2$ and $LIVO_2$ saturation is compared to the average of the two measurements. This analysis of the agreement between the two measurements generates an estimate of the bias and precision between the measurements. A fairly wide distribution of values is expected due to different perioperative loading conditions and other situations e.g., paralysis, body temperature and bleeding ($LIVO_2$ saturation range from 45%-85% saturation is likely).

EXAMPLE 4

Optoacoustic Determination of $S_{LIV}O_2$ in Healthy Volunteers During Induction of Lower Body Negative Pressure (LBNP) to Simulate Hypovolemic Shock In certain embodiments, clinical validation protocols using LBNP are used to establish efficacy of a device and method for ultrasound guided optoacoustic monitoring of oxygen saturation. In one such validation protocol, optoacoustically measured $S_{LIV}O_2$ is compared to SVC blood, obtained from an oximetric pulmonary artery ("PA") catheter infusion port, at each LBNP stage to demonstrate the feasibility and accuracy of noninvasive monitoring of LIV saturation. $S_{IJV}O_2$ during each LBNP stage as a surrogate for brain oxygenation is also done. Simultaneous measurement of the $S_{LIV}O_2$ and $S_{IJV}O_2$ in healthy volunteers will determine the venous oxygenation gradient and provide information on hemorrhage compensation and tolerance.

Lower body negative pressure ("LBNP") to simulate hypovolemic shock has been used as a research tool since 1965 and is considered to simulate conscious hemorrhage volumes of up to 1500 mL. LBNP allows for a graded response e.g., the magnitude of suction can be increased or decreased by adjusting the vacuum motor. In certain embodiments, subjects are placed supine and only the subject's iliac crest and lower extremities are enclosed in the negative pressure chamber. The tight enclosure allows for the development of negative pressure or suction. As the negative pressure is applied, blood in the lower extremities is "trapped", which simulates hypovolemia. Since the subject is supine with lower body resting on a seat, it is easier for the subject to remain still/relaxed and thus minimizing the influence of the muscle pump on venous return. The amount of negative pressure can be adjusted to simulate varying levels of hypovolemia. During step-wise LBNP, there is a progressive redistribution of blood volume from the central to the lower regions of the body. Physiologic compensation of hypovolemia includes activation of the cardiopulmonary and arterial baroreceptors, resulting in an increase in heart rate and sympathetic nerve activity to maintain central perfusion. Release of the negative pressure rapidly normalizes the circulation.

FIG. 11 depicts hemorrhage classifications based on determinations of venous oxygenation. Traditional estimates of blood loss rely on vital signs, which are often late findings. In the embodiment depicted in FIG. 11, venous oxygen saturation and gradient [difference between central perfusion e.g., IJV saturation and peripheral e.g., LIV saturation] are employed to approximate volume loss severity and physiologic compensation.

Use of Venous Oxygenation to Determine Hemorrhage Severity: It has long been recognized that hemorrhage causes an inadequate delivery of oxygen delivery to the tissues, due to lower Hgb and decreased cardiac output. Strong compensatory mechanisms are initiated at the onset of blood loss and hypovolemia. Activation of the autonomic nervous system, in particular sympathetic nervous system, results in blood flow centralization in order to secure perfusion of brain and heart, since these organs cannot tolerate an interrupted supply of oxygen delivery. Conversely, sympathetic vasoconstriction leads to a reduction in perfusion of peripheral organs such as skin and muscle, which can adapt for longer periods of time with substantially lower blood flow, albeit at the expense of a lower tissue oxygen content. The amount of oxygen utilization can be estimated from the venous effluent oxygen content for each tissue. Specifically, the amount of oxygen in the regional venous system provides a direct gauge of perfusion to that organ.

For example, the amount of oxygen in the internal jugular vein is an index of brain perfusion, whereas the innominate vein oxygenation is an index of the upper thoracic cavity, which has significant muscle mass.

Figure 12:
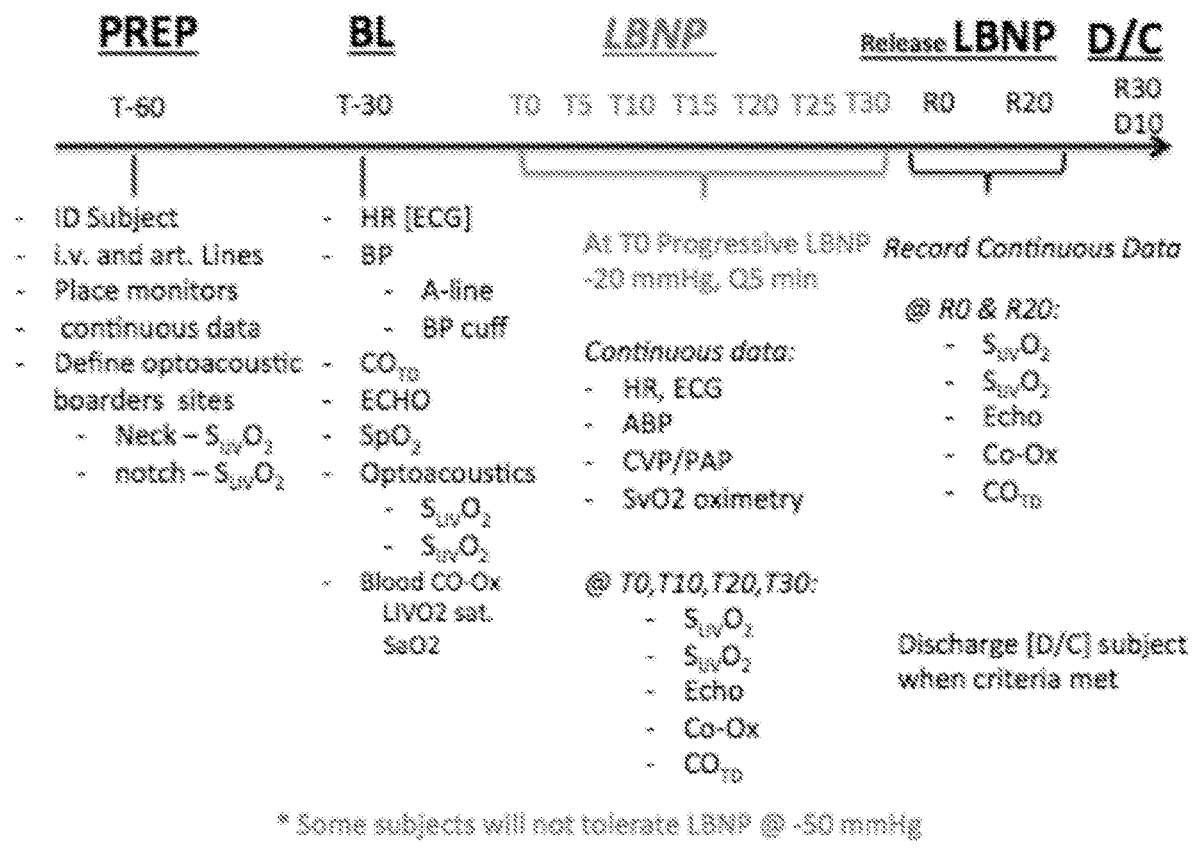

In certain embodiments, further clinical validation protocols are used to establish efficacy of a device and method for ultrasound guided optoacoustic monitoring of oxygen saturation to confirm that by measuring the venous oxygenation from a centralized source such as IJV and a source representing peripheral tissues such as LIV along with its differential gradient (centralized minus peripheral tissues), novel data is collected on hemorrhage severity of hemorrhage and its compensatory physiologic response (FIG. 12). Conceptually, due to vasoconstriction, peripheral venous oxygenation will precipitously decrease as hemorrhage severity is increased, whereas, centralized venous oxygen is preserved until later stages of hemorrhage. The venous oxygenation gradient would therefore be increased during the compensatory phases. As hemorrhage severity continues, centralized flow becomes compromised. At this point, saturation in IJV declines and the gradient becomes pseudo-normalized. The actual values will be tested in human subjects during LBNP.

FIG. 12 depicts an example of a clinical validation protocols used to establish efficacy of a device and method for ultrasound guided optoacoustic monitoring of oxygen saturation. After instrumentation and baseline, progressive LBNP will be induced over 30 min and then released. Continuous hemodynamic measurements, oxygenation measurements [hemoximetry and optoacoustics] and echocardiography will be performed.

Instrumentation, procedures and measurements: Specifically, on the day of the human study, subject will be placed supine on a specialized mattress with their lower body sealed at the iliac crest inside the lower body negative pressure chamber. An 18 gauge peripheral i.v. catheter is placed in a hand or arm vein. A 20 gauge angiocatheter is inserted into the radial artery to measure arterial oxygenation $SaO_2$ and blood pressure, after an Allen's test to ensure radial and ulna collateral flow. Catheters are placed aseptically and secured in place with tape. After a sterile prep and drape and infiltration of local anesthesia, an oximetric pulmonary artery ("PA") catheter (PreSep Edwards LifeSciences Irving CA) is placed under ultrasound guidance in the left internal jugular vein via lateral border of the sternocleidomastoid muscle. Confirmation on pulmonary artery placement is assured via progression of right ventricular waveform, followed by a pulmonary waveform and lastly an occlusive pressure [PAOP] waveform when the balloon is inflated. After PAOP waveform is confirmed, the PA catheter is secured such as via suture. A thermodilution cardiac output ($CO_{TD}$) is performed to ensure confirmation that the curve has a right ventricular ejection pattern. All catheters are kept patent throughout the protocol with sterile saline solution in a pressurized bag.

In certain embodiments, throughout the entire protocol the variables are measured continuously including one or more of: invasive mean arterial blood pressure (MAP) via the arterial line, peripheral venous pressure (PVP), heart rate (HR) measured via an electrocardiogram (ECG; General Health Care), central venous pressure (CVP), pulmonary artery pressure (PAP), oximetric pulmonary artery saturation ($SvO_2$) and blood temperature. Ultrasound is used to mark the sites and define borders for target veins such as for example the IJV and LIV in order to more efficiently approach the target vessels for optoacoustic measurement. In brief, the optoacoustic probe are placed in the suprasternal notch to measure innominate vein $S_{LIV}O_2$ as described. An additional probe is placed on the lateral border of the sternocleidomastoid muscle to measure internal jugular vein saturation ($S_{IJV}O_2$). Echocardiography and hemoximetry is performed at time points described in FIG. 12.

T-30: Baseline: thirty min before LBNP, (T-30), baseline data is recorded including; HR, Temp, MAP, oximetric $SvO_2$, CVP, COTD and $SpO_2$. Blood (1 mL each) samples from the PA catheter infusion port [LIV $O_2$ sat] and radial artery [$SaO_2$] is measured via co-oximetry (Instrumental laboratories, Orangeburg NY). Systolic function and diastolic function is measured using echocardiography. Optoacoustic measurements ($S_{LIV}O_2$ and $S_{UV}O_2$) are performed.

T0: LBNP: actively results in a progressive redistribution of blood volume from the central to the lower regions of the body, inducing relative hypovolemia thus causing a hypotensive challenge. Tolerance to simulated hemorrhage shows a wide inter-individual variety. Measurements are taken at dedicated time points. At T0, subjects are exposed to a graded simulated hemorrhage using LBNP. The sealed LBNP chamber is connected to a vacuum motor, which when activated, causes a progressive redistribution and pooling of blood in the lower extremities. Subjects undergo progressive stages of negative pressure by increasing the vacuum by 10 mmHg every 5 min. Thus, the first LBNP stage (T0) will start at −20 mmHg and at T5 LBNP will be advanced to −30 mmHg until T30, in which the LBNP will advance to −80 mmHg. The LBNP experiment ends when the following occur: 1) the subject completes 5 min of −80 mmHg (at T35); 2) hemodynamic decompensation e.g., systolic blood pressure less than 75 mmHg or exaggerated fall in systolic BP>15 mmHg in 5 min or paradoxical bradycardia; or 3) physiologic decompensation occurs e.g. symptoms of light headiness or confusion (pre-syncope) or visual abnormalities (blackout, tunnel vision or loss of color), diaphoresis, nausea and dizziness. Based on literature, 50% of subjects are unable to tolerate a LBNP of −60 mmHg.

All subjects are monitored continuously for cardiovascular changes and encouraged to express discomfort. The release of the LBNP results in the pooled blood into the circulation and rapid recovery. Cardiovascular parameters during and after LBNP are monitored. For stability purposes, the subjects are observed for a further period such as for example another 30 min before they are discharged.

Recovery [R0]: defined as the time at which LBNP is turned off, which represents the time of decompensation or non-tolerance or T35 @−80 mmHg for 5 min. Measurements also taken at R10: 10 min of recovery and R20: 20 min of recovery [Final measurements].

Discharge: At D0 all lines will be removed and at D30, the subject is discharged.

Hemodynamic measurements: are recorded at time points such as T-60, T-30, T0, T5, T10, T15, T20, T25, T30, R0, R10 and R20—before discharge.

Arterial and venous Pressure: Continuous beat-by-beat arterial blood pressure is recorded invasively via a catheter in the radial artery. Mean arterial blood pressure (MAP) is calculated and recorded. Arterial blood pressure is digitally displayed and recorded at 1000 Hz via intra-arterial catheter transducer. Event times are noted and recorded on Powerlab software. The arterial catheter is also be used to measure arterial oxygenation ($SaO_2$) at specified time points. Similarly, a transducer is used to continuously measure CVP from the Pre-Sep catheter.

Electrocardiography (ECG—heart rate): A normal clinical 3 lead ECG is placed on the subject's chest during the experimental procedure.

Temperature: Core blood temperature is obtained from the Pre-Sep catheter.

Pulse oximetry: Continuous pulse oximetry ($SpO_2$), perfusion indices (PVI and PI) and non-invasive Hgb—are continuously measured. The determinants provide which arterial blood saturation and perfusion.

Cardiac output (CO): is determined by thermodilution (injection of saline into proximal port and reading the thermodistribution from the distal port) from the PA catheter. Measurements are used to calculate systemic vascular resistance (SVR: dynes.sec.cm-5) as follows:

$$SVR=[MAP-CVP]/CO \times 80$$

Oxygen delivery ($DO_2$) will be calculated from CO, Hgb and $SO_2$ as:

$$DO_2 = CO \times Hgb \times 1.3 \times SO_2$$

Ventricular volume and function by echocardiography provide an independent measure of preload at different LBNP stages and upon immediately cessation of LBNP. In certain embodiments, eligibility for the studies includes demonstration of good cardiac imaging in the two-chamber apical view. Where volunteers are young, free of cardiac disease, and have no regional wall motion abnormalities, it is anticipated that quantitatively reliable information from the two-chamber, apical view, will be obtained using the modified Simpson's rule to measure ventricular volume. End-diastolic (EDV) and end-systolic volume (ESV) measurements is obtained from a transducer and ultrasound system. A 3.5 MHz transducer and ultrasound system (Vivid 7 PRO BT04, GE Medical Systems, Milwaukee, WI) provides ultrasound location data in one embodiment. Left ventricular (LV) area and length is obtained from the parasternal LV long axis and used for volumetric calculations. In certain embodiments, the modified Simpson's rule is applied for calculating EDV, ESV, stroke volume (SV) and ejection fraction (EF %). Measurements are determined at all specified time points.

Co-oximetry for arterial and venous oxygenation: In certain embodiments, blood is sampled from arterial ($SaO_2$) and venous catheters ($SvO_2$) at time points including T-30, T0, T10, T20, T30, R0 and R20 and measured using a co-oximeter. In certain embodiments, a volume, such as for example, 1 mL, of blood is removed from arterial and venous catheters, which are connected to the transducers.

Non-invasive optoacoustic determination of Venous Saturation: After mapping location using surface ultrasound, an optoacoustic probe is placed in the lateral border of the left suprasternal notch to measure the $S_{LIV}O_2$. A second optoacoustic probe is positioned on the left lower anterior triangle to measure $S_{UV}O_2$. For each time point outlined (FIG. 12), signals generated over a 75 second window are averaged. The mean±SD for each measurement set is compared to venous hemoximetry samples. The $S_{LIV}O_2$ and $S_{LIV}O_2$ and gradient is also used to estimate hemorrhage severity and compensatory response.

Statistical considerations and data analysis: Statistical analysis is performed. Descriptive statistics are used such as for the analysis of the mean and standard error of the mean. A regression analysis is done for optoacoustic measurements versus hemoximetry. Analysis of dependent variables is determined as the effect of LBNP on each measured/calculated physiological variable e.g., change in the measured variable during LBNP to normal pressure and tolerance e.g., LBNP off. Analyses to be utilized may include independent student t-tests (i.e. "LBNP" vs "no LBNP") and two-way analysis of variance tests (ANOVA; i.e. different time-points for comparison "LIV" vs "IJV"). If an interaction is identified by the two-way ANOVA an appropriate multiple comparison post-hoc analysis is performed. The alpha level for all analyses will be set at $P<0.05$.

EXAMPLE 5

Optoacoustically Measured $S_{LIV}O_2$ Correlates with Simultaneous Measurements Hemoximetry Derived $S_{SVC}O2$ at Each LBNP Stage and Recovery In certain embodiments, further clinical validation protocols are used to establish efficacy of a device and method for ultrasound guided optoacoustic monitoring of oxygen saturation. In one embodiment, an optoacoustic technique is applied to compare sets of data at various time points by linear regression (optoacoustic $S_{LIV}O2$-Y-axis versus hemoximetry $S_{SVC}O2$ saturation-X-axis). A Bland-Altman approach may be performed. In human clinical validation protocols, a very good correlation is demonstrated clinically. In certain tests, the target lower body negative pressure ("LBNP") stage is targeted for −80 mmHg, which elicits pre-syncope or significant hypotension in 90% of the subjects, and which is anticipated to result in significant central venous desaturation (values<50%). Values of sensitivity, specificity and positive predictive value are obtained. While the adequate sample size for comparative studies is difficult to determine, especially based on the assumption that the two measurements are expected to have little difference between them, the LBNP is expected to yield marked differences in venous saturation during different phases. Therefore, requisite data points will be obtained to provide a broad range based on individual variability as well as baseline to pre-syncope as a model of real-world circumstances.

EXAMPLE 6

Simultaneous Measurement of the $S_{LIV}O_2$ and $S_{LIV}O_2$ to Determine the Venous Oxygenation Gradient In certain embodiments, further clinical validation protocols are used to establish efficacy of a device and method for ultrasound guided optoacoustic monitoring of oxygen saturation to rapidly assess venous oxygenation changes that occur during a progressive simulated hemorrhage. It is expected that initially the lower body negative pressure ("LBNP") will generate a greater differential (increased venous oxygenation gradient) between the peripheral and central venous oxygenation. It is further expected that subjects that have poor tolerance to LBNP will have lower $S_{UV}O_2$ versus $S_{LIV}O_2$ at baseline and a more rapid decent in $S_{LIV}O_2$ at early LBNP settings.

It is noted that cardiovascular response is more rapid than metabolic changes. Decompensation e.g., hypotension or inappropriate bradycardia can rapidly (seconds) occur in LBNP. Venous oxygen desaturation occurs when perfusion is reduced. This process takes minutes. While blood pressure is maintained due to compensatory increases in peripheral resistance, skeletal muscle mass (likely represented by $S_{LIV}O_2$) will continue to have low oxygen delivery and therefore oxygen debt increases leading to lower $S_{LIV}O_2$. Therefore, it is expected that $S_{LIV}O_2$ will likely continue to fall during the compensatory phase (venous oxygen gradient sub-hypothesis) even as it could be difficult to predict when decompensation phase occurs. Likewise, $S_{UV}O_2$ may not decrease during LBNP but may become reduced after recovery (re-perfusion).

Provided herein is a novel, noninvasive, optoacoustic monitoring system that measures key indices of oxygenation that are altered with shock and TBI. Also provided are clinical validation protocols that establish efficacy of a device and method for ultrasound guided optoacoustic monitoring of oxygen saturation. In certain embodiments, human clinical trials are undertaken to evaluate the predictive value of $S_{LIV}O_2$ to diagnose shock and guide resuscitative therapy so that under and over-resuscitation do not occur. In certain embodiments, complementary determination of $S_{LIV}O_2$ are also performed, which may provide: 1) new information on hemorrhage compensation 2) critical brain oxygenation data in patients with TBI. In certain embodiments, the $SO_2$ data provided by the method and apparatus disclosed herein is used in conjunction with other modalities including: optimizing positive end-expiratory pressure ("PEEP") [$SpO_2$ vs $S_{LIV}O_2$]; selecting vital fluid choices such as the need for blood transfusion vs other fluids; reducing oxygen consumption needs (considerations of the degree of fever and shivering vs a need for paralysis fluid and sedation and anesthesia); and duration and/or position of resuscitative endovascular balloon occlusion of aorta ("REBOA") to modulate proximal vs distal venous oxygenation.

EXAMPLE 7

Probe Operational Modes and Apparatus Examples

Mode 1: Sequential use of ultrasound guidance and optoacoustic measurement. In this sequential mode, first an ultrasound imaging (or Doppler measurements) is performed to localize a blood vessel of interest. Once the optimal location for monitoring of central venous oxygenation is identified, the optoacoustic probe is applied to provide oxygenation measurements of the identified blood vessels. The successive approach can be visual, i.e. visual identification of the target vessel with ultrasound image first, then optoacoustic measurements with an optoacoustic probe. FIG. 13A shows an optoacoustic probe that has been tested in CABG patients.

Optoacoustic probes can be used in succession with various types of ultrasound probes. The ultrasound imaging probe i12L-RS (GE) was tested for vessel localization in conjunction with a GE Vividi system in the studies described in EXAMPLE 2. The GE ultrasound imaging probe i12L-RS has a wide frequency band of 5-13 MHz. Other U/S probes that have been tested successfully including the Doppler probe IPP3 having a frequency of 8 MHz and the Doppler probe VP4HS having a frequency of 4 MHz but these particular U/S probes are given only as non-limiting examples.

A specially designed holder (patient interface) is preferably used for this purpose. The ultrasound probe is inserted in the holder and after the ultrasound procedure, the probe is removed from the holder and an optoacoustic probe is inserted in the holder to probe the blood vessel with high resolution and accuracy. The holder structure allows for sequential use of the ultrasound probe and optoacoustic probe at the same tissue site. The axis of the optoacoustic probe may coincide with that of the ultrasound probe. Using this mode, we performed ultrasound-guided optoacoustic monitoring of blood oxygenation in the innominate and other veins. This mode and data generated thereby was demonstrated in EXAMPLE 2 herein.

In certain embodiments, disposable adapters or patient interfaces are provided for successive (or iterative) use of ultrasound and optoacoustic probes. FIGS. 13B-13D show an example of use of such an adapter. As shown in FIG. 13B, the geometry of the adapter 50 allows for holding and inserting ultrasound and optoacoustic probes successively in the same location on the patient. First as depicted in FIG. 13D, an ultrasound probe (52) nestled into adapter (50) is used to find the blood vessel of interest. Once the blood vessel is found and optimal location of the optoacoustic probe is identified, adapter (50) is attached to skin of the patient at the optimal location using a medical adhesive or tape. Then, as shown in FIG. 13E, the ultrasound probe is removed from the adapter and the optoacoustic probe (54) is inserted in the holder. As depicted in FIG. 13C, holder (50) includes a space (51) dimensioned to approximate and securely hold ultrasound probe (52) depending on the geometry of the probe. Also as depicted in FIG. 13C, holder (50) also includes a space (53) dimensioned to approximate and securely hold an optoacoustic probe depending on the geometry of the probe. The exemplified ultrasound probe (52) is GE i12L-RS intraoperative linear probe (General Electric, Milwaukie WI) and includes a sloping "wand" like handle (56). Thus, as depicted in FIGS. 13B and 13C, holder (50) includes a sloping rest (57) that further customizes the holder to the geometry of the probe to be used. Because the axis of the optoacoustic probe is aligned with axis of the ultrasound probe using the holder, the optoacoustic detection of the blood vessel signals is optimal when the optoacoustic probe is inserted in the adapter. After the procedure, the adapter can be disposed of.

Mode 2: Dual mount ultrasound guidance and optoacoustic measurement apparatus. In the dual mount mode, both ultrasound probe and the optoacoustic probe are mounted together in a holder and once the blood vessel of interest is identified and localized with the included U/S probe, optoacoustic measurements are performed with the optoacoustic probe. Ultrasound imaging and optoacoustic measurements can also be performed simultaneously and continuously. The axis of the optoacoustic probe can be parallel to the axis of the ultrasound probe. Alternatively, the axis of the optoacoustic probe can be adjusted at some angle with respect to the axis of the ultrasound probe to provide accurate probing from a specific depth in tissue, in particular, from the depth of the blood vessel of interest.

Figure 14A:
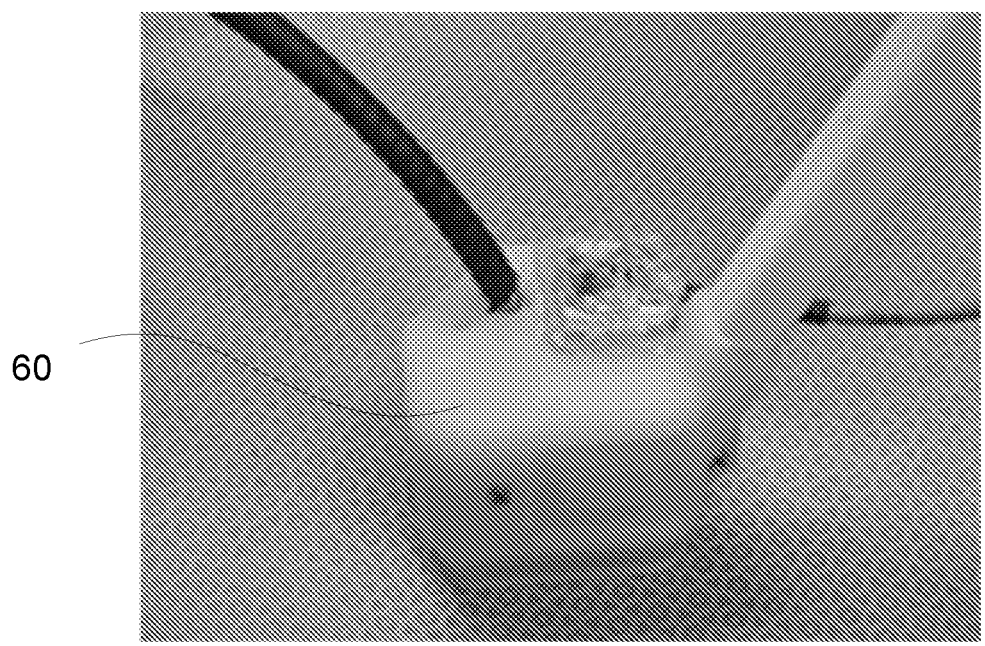
FIG. 14A-FIG. 14B depict a working prototype embodiment of a combined ultrasound imaging and optoacoustic monitoring probe.
Figure 14B:
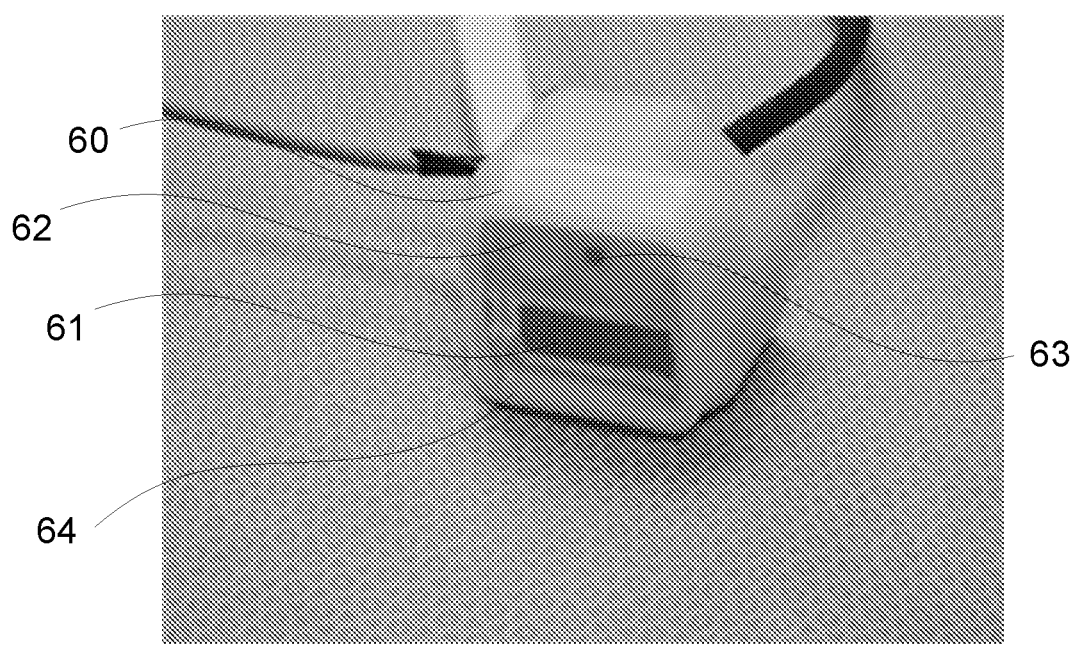

FIGS. 14A-14B depict combined ultrasound imaging and optoacoustic monitoring probes. An ultrasound imaging probe, specifically depicted is a Vivid e, i12L-RS (GE) U/S probe, is combined in one casing (60) with a miniature optoacoustic probe. The elements of the dual apparatus can be seen FIG. 14B showing the ultrasound probe face (61) and an optoacoustic probe with a sensitive element, larger circle (62), and optical fiber (63) for light delivery (the smaller dark circle). The bottom part (64) of the combined probe has an indentation which can be filled with a molded gel pad for acoustic matching to tissues.

Figure 15A:
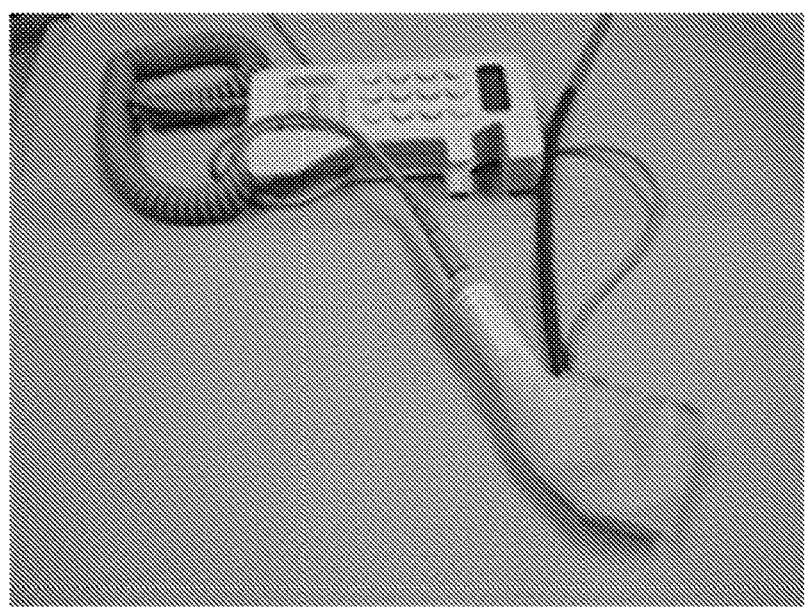
FIG. 15A-FIG. 15C depict combined ultrasound and optoacoustic monitoring probes wherein a Doppler ultrasound system is adapted combination with for optoacoustic monitoring.
Figure 15B:
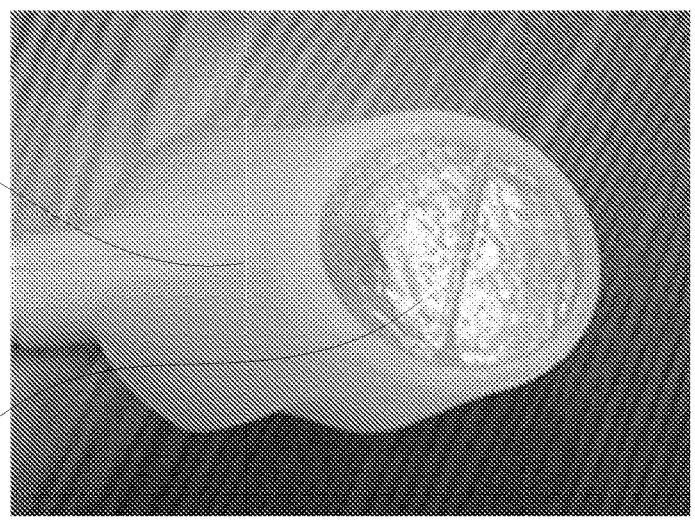
Figure 15C:
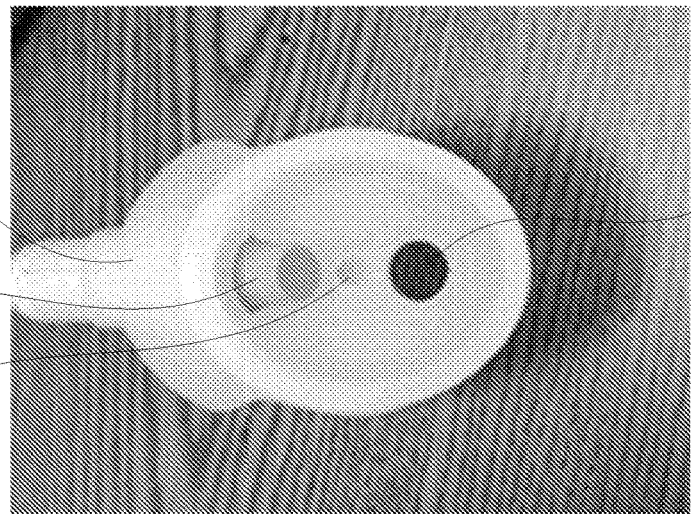
Figure 15D:
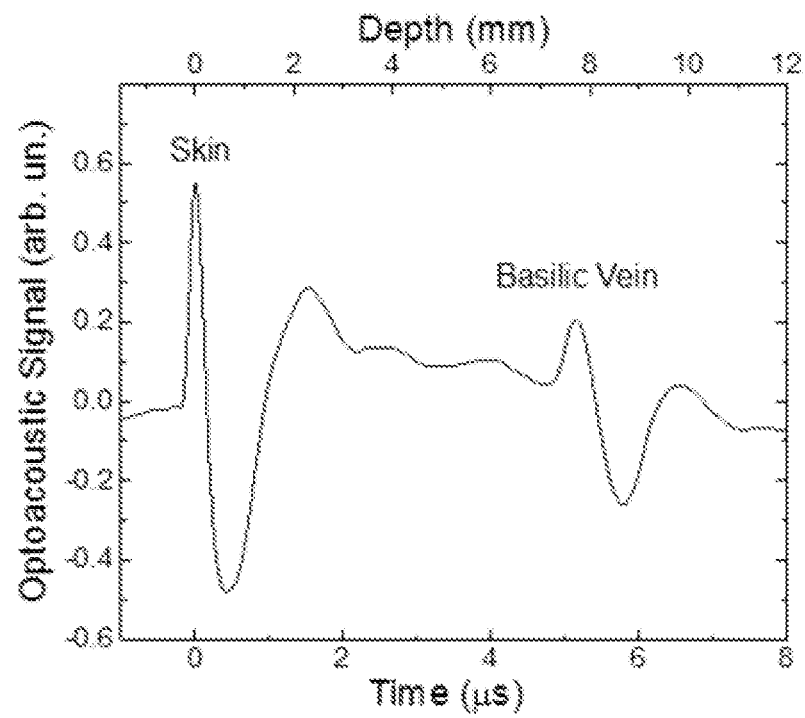
FIG. 15D show optoacoustic signals obtained with the combined Doppler and optoacoustic device depicted in FIG. 15A.
Figure 15E:
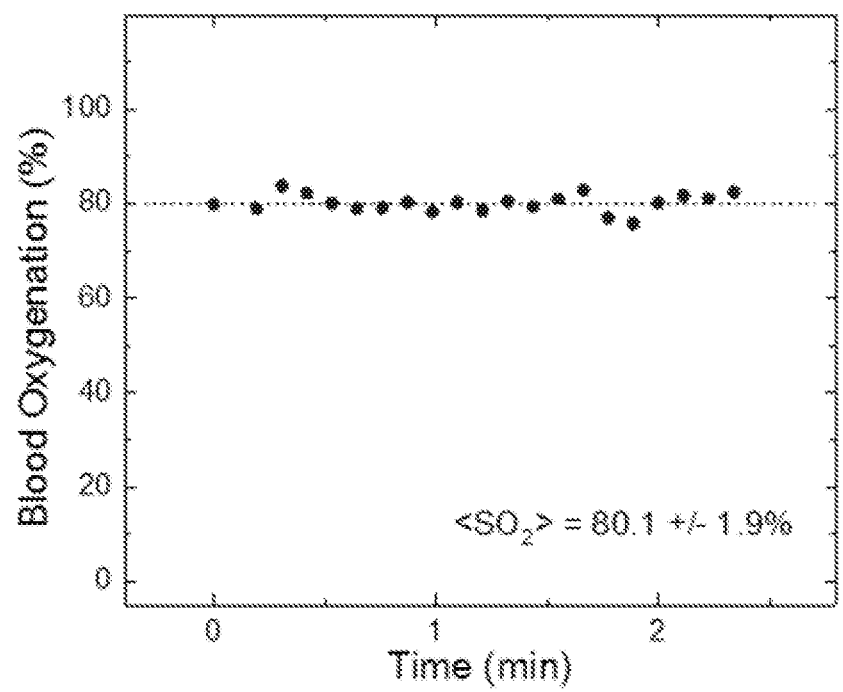
FIG. 15E shows corresponding blood oxygenation values obtained with the device depicted in FIG. 15A.

FIGS. 15A-15C depict combined ultrasound imaging and optoacoustic monitoring probes wherein a Doppler ultrasound system is adapted combination with for optoacoustic monitoring. In the depicted example of FIG. 15A, a combined instrument prototype is shown that has been constructed from a handheld Doppler ultrasound system (Model MD2 VP4HS (4 MHz probe, Huntleigh Technology Plc.) combined with an optoacoustic system by adding a light source and an optoacoustic transducer. As shown in FIG. 15B, the bottom part of the combined probe housing (70) can be covered with a molded gel pad (72). The casing of the combined probe allows for use of either a bigger Doppler probe such as one like the VP4HS depicted (74). Alternatively a pencil-like probe IPP3 (not shown) can utilized and securely mounted in the combined probe FIG. 15C. The optoacoustic transducer is inserted into hole (78). A pulsed laser light source will also be mounted in the housing for optoacoustic stimulation through hole (76). Using this prototype probe, optoacoustic signals and blood oxygenation in basilic vein were measured as shown in FIGS. 15D-15E. FIG. 15D shows an optoacoustic signal recorded from the basilic vein after it was detected with the Doppler probe. Continuous optoacoustic monitoring of the basilic vein oxygenation is presented in FIG. 15E. The average blood oxygenation detected and the standard deviation were 80.1% and 1.9%.

Figure 16A:
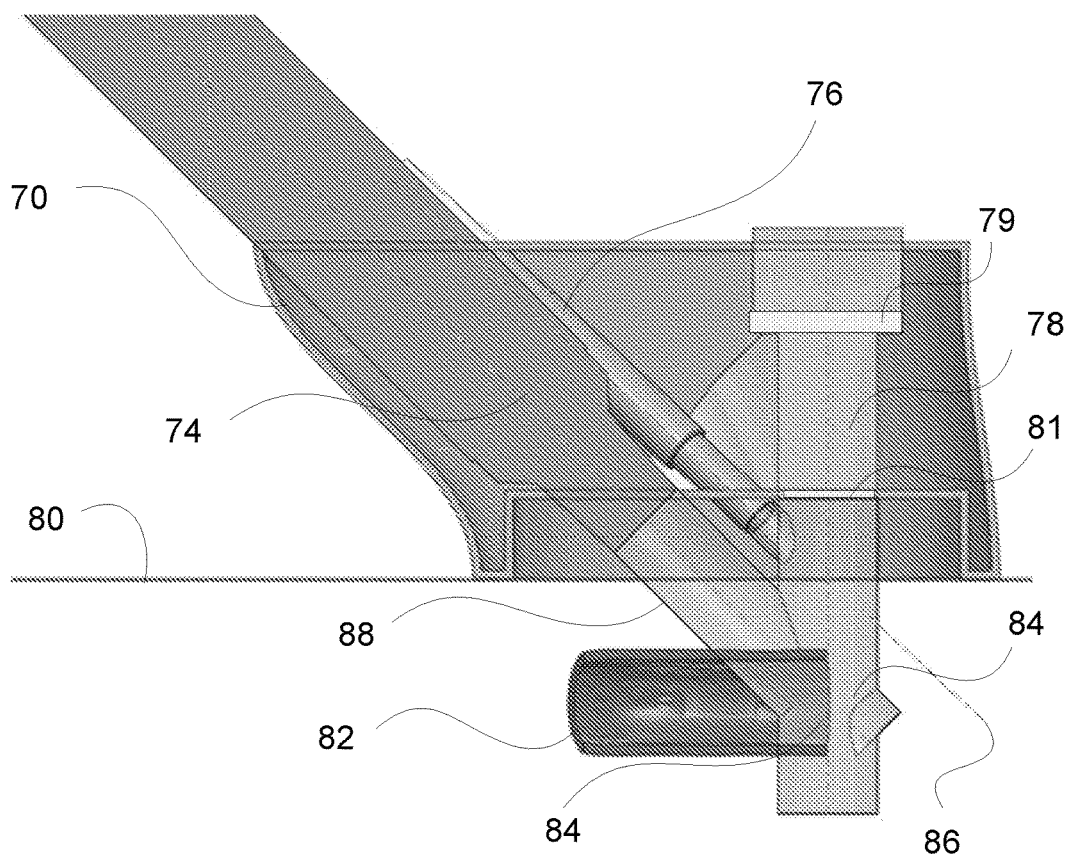
FIGS. 16A and 16B show side and oblique views respectively of embodiments of dual mount Doppler ultrasound guidance and optoacoustic measurement apparatus.
Figure 16B:
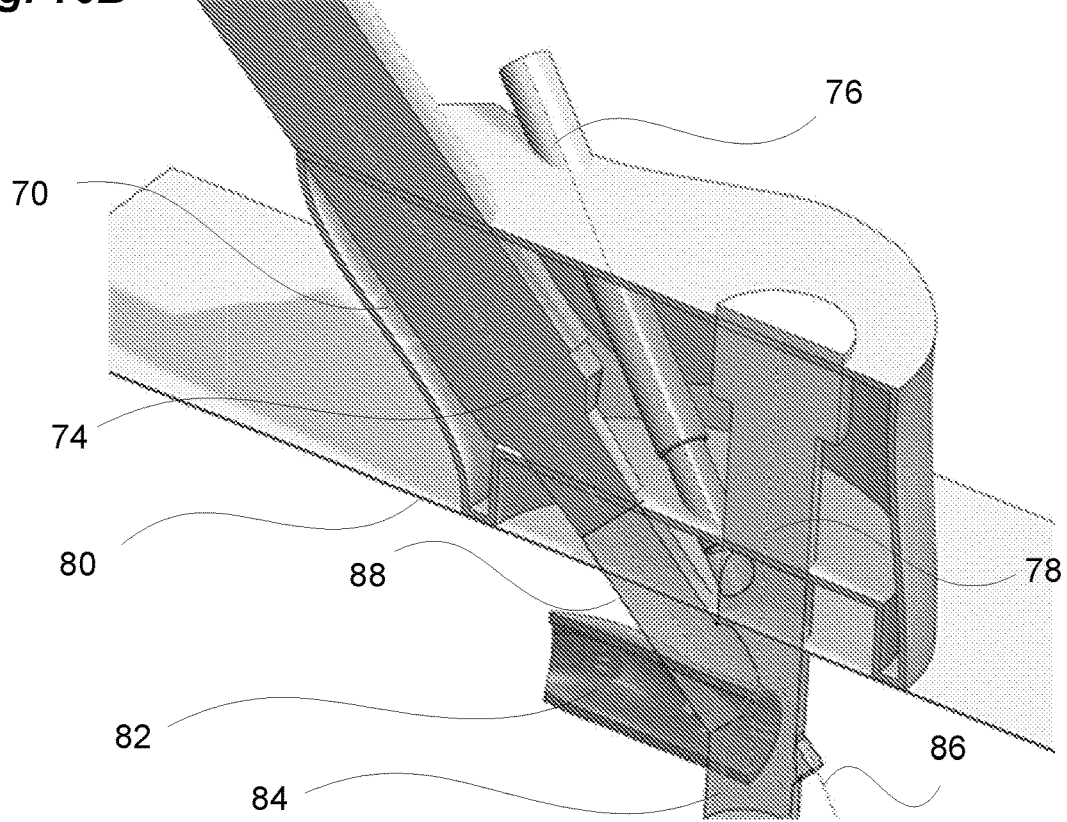

FIG. 16A-16B show side and oblique views respectively of two embodiments of dual mount ultrasound guidance and optoacoustic measurement apparatus. In both cases, holder (70) securely mounts ultrasound probe (74), light source (76) and optoacoustic probe (78). The optoacoustic probe (78) may include a printed circuit board (79) and other electronics. The face of the optoacoustic transducer is protected by a film (81) such as for example a polyguard film of 5-15 mil. In some embodiments the film is 10 mil. The skin of the patient is figuratively shown as (80) and the paths of investigation of the vein (82) by ultrasound field (88), optoacoustic stimulating light path (86) and optoacoustic investigation field (84). In FIG. 16A, the probes are positioned in the same plane and aligned at a specific angle to one another to provide optoacoustic probing from a specific depth and accurate measurement of blood oxygenation from this depth.

FIG. 16B depicts another embodiment of a dual ultrasound (or Doppler) probe and an optoacoustic probe. The probes are positioned in different planes and aligned at a specific angle to provide optoacoustic probing from a specific depth and accurate measurement of blood oxygenation from this depth.

Figure 16C:
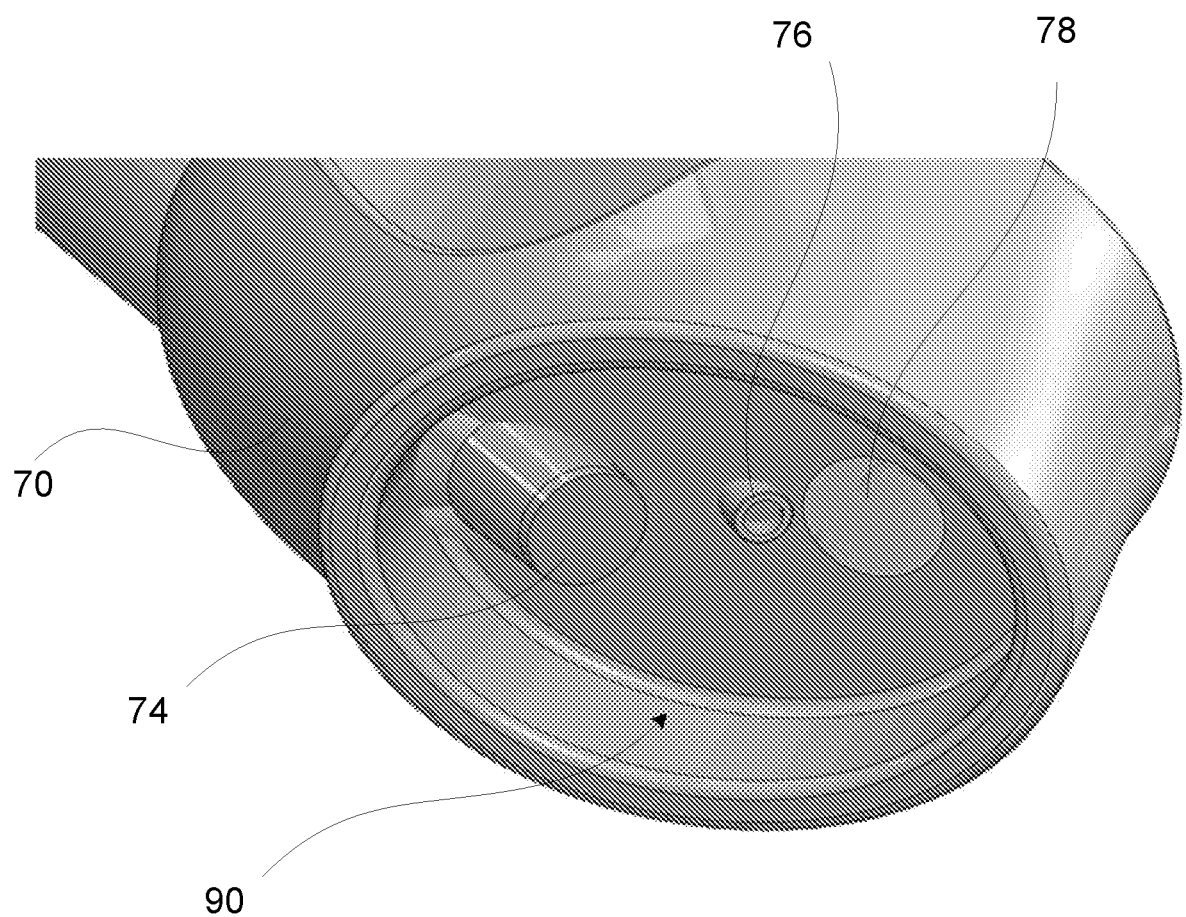
FIG. 16C shows an oblique bottom view of an embodiment of a dual mount Doppler ultrasound guidance and optoacoustic measurement apparatus.

FIG. 16C shows an oblique bottom view of an embodiment of a dual mount ultrasound guidance and optoacoustic measurement apparatus showing holder (70) securely mounting ultrasound probe (74), light source (76) and optoacoustic transducer (78). In the depicted example, holder (70) includes a hollow interior space (90), within which the internal components of the probe reside. In certain embodiments the hollow interior space is designed to be filled with an acoustic gel that contacts both the ultrasound and optoacoustic sensors.

An acoustic backing material may be positioned in the holder behind the optoacoustic transducer. It provides backing for the sensor (for wideband detection of pressure waves) and absorbs the vibrations that travel through the sensor to prevent undesired ringing in the signal and separate part of the signal from ringing noise. In some embodiments, the attenuator comprises a mass of a plastic material such as an epoxy material.

FIG. 17 provides engineering drawings of an embodiment including holder (70) which securely mounts ultrasound probe (74), fiber optic cable transmitting light (92) and optoacoustic probe (78). Also included in the depicted embodiments is a fill tube (93) for filling and refilling cavity (90) with acoustic gel.

Mode 3: Both ultrasound imaging and optoacoustic measurements are performed using the same ultrasound detector/array. In this shared mode, first ultrasound imaging is performed using the ultrasound array. Then, light pulses directed to the blood vessel of interest generate optoacoustic waves in the blood vessel and these optoacoustic waves are detected by the ultrasound array. Co-utilization of an ultrasound imaging probe as a detectors of optoacoustic waves provides both ultrasound guidance for monitoring and detect optoacoustic waves induced in tissues (including blood vessels) by the optical sources. First, the blood vessel of interest is found using the standard ultrasound imaging mode which is based on generating ultrasound in the probe, directing it to the tissue, and detecting ultrasound echo signals from the tissues. Once the blood vessel is found, optical radiation is directed to the tissue. The optoacoustic waves generated in tissues propagate to the ultrasound probe and the ultrasound-sensitive detectors of the ultrasound probe detect the optoacoustic waves from the tissue. Then the optoacoustic signals are recorded and analyzed by the ultrasound system to display oxygenation.

Although each of these modes has advantages and drawbacks, they all can be used for ultrasound-guided optoacoustic monitoring depending on a specific application, position of the blood vessel, and its geometry. Whether used in any one the modes, in certain embodiments, ultrasound in a frequency range of 1-18 MHz is utilized for location of the vessel to be tested for oxygen saturation by optoacoustics. In other embodiments, the ultrasound in a frequency range of 4-13 MHz is utilized for location of the vessel to be tested for oxygen saturation by optoacoustics. In certain embodiments, ultrasound at a frequency 13 MHz±1 MHz is utilized for location of the vessel to be tested for oxygen saturation by optoacoustics.

Note that the term "Doppler" is used herein interchangeably with ultrasound (U/S) as Doppler utilizes ultrasound. "Doppler" has become synonymous with "velocity measurement" in medical imaging but as used herein, Doppler is used interchangeably with ultrasound. Where the term "Doppler" is used herein, it is because the U/S probe is specifically adapted to have velocity measurement capabilities although this is not required. Ultrasound imaging systems typically also have Doppler capabilities so they provide both ultrasound imaging and velocity measurements in blood vessels in the images. The Doppler system in FIG. 15 is not an imaging system, it provides audible signals without images when its probe is directed to a blood vessel. So, using this audible signal, one can direct optoacoustic probe in optimal direction and at optimal location in the body. Imaging can be employed if desired.

Many optical sources with wavelengths suitable for oxygenation measurements can be used in the optoacoustic systems, including but not limited to: optical parametric oscillators (OPOs), laser diodes, light emitting diodes (LEDs), dye lasers, and solid state lasers (such as Nd:YAG laser, Alexandrite laser). In certain embodiments, the light source may comprise one or more laser diodes or light emitting diodes. The light source of the monitor may be configured to generate light having an energy of 1 µJ to 1 mJ. The light source of the monitor may be configured to generate light having wavelengths in range of two or more of 685-715 nm, 715-745 nm, 745-775 nm, 790-820 nm, or 845-875 nm, such as two or more of 700 nm, 730 nm, 760 nm, 800 nm, 805 nm, or 860 nm, for example. Light from the source is conveyed such as via cables that comprise one or more optical fibers configured to direct light generated by the light source to the light output of the probe head.

Many acoustic detectors can be used in the optoacoustic systems, including but not limited to: piezodetectors that are based on piezomaterials such as piezopolymers and piezoceramics, capacitive micromachined ultrasonic transducers (CMUTs), and optically-based ultrasound detectors such as interferometric detectors, optical beam deflecting detectors, pressure-sensitive optical elements. In certain embodiments, the acoustic detector may further comprise an amplifier for the acoustic transducer. The probe head may further comprise an electromagnetic shield that shields the acoustic sensor and amplifier from electromagnetic interference. The probe head may further comprise an acoustic attenuator configured to absorb undesired ringing in the probe head.

In some embodiments, the acoustic detector comprises a piezoelectric transducer that uses the piezoelectric effect to measure changes in pressure, acceleration, strain, or force and convert them into an electrical signal. The sensor may be separated from the electromagnetic shield by a spacer element, which can be made of a polymeric material, such as polyamide. In some embodiments, the spacer element is approximately 0.005 to 5 mm thick.

The electrical signals generated by the acoustic sensor are transmitted to a Printed Circuit Board ("PCB") via one or more electrical wires. The PCB includes a preamplifier that amplifies the signals received from the sensor before transmitting them to a monitor or computer of the system along further electrical wires. The preamplifier can be configured to provide about 40 dB of gain at about 500 kHz, having a bandwidth of about 3 dB in the range from about 40 kHz to about 10 MHz. The PCB may further comprise a digitizer configured to digitize the acoustic signal detected by the acoustic sensor. For example, the digitizer can be configured to sample the acoustic signal from the preamplifier at least at about 20 MHz, in response to a trigger signal from the laser diode subsystem connected to the probe, as described herein. The digitizer can, for example, store about 1000 samples of the acoustic signal, and transfer the block of samples to the processor of the console unit connected to and controlling the operation of the optoacoustic probe, for waveform averaging of the samples. An acoustic backing material may be positioned behind the acoustic sensor. It provides backing for the sensor (for wideband detection of pressure waves) and absorbs the vibrations that travel through the sensor to prevent undesired ringing in the signal and separate part of the signal from ringing noise. In some embodiments, the attenuator comprises a mass of epoxy. A hollow interior space, within which the internal components of the probe reside, may be substantially cylindrical, with a diameter in a range from about 8 to about 10 mm, and a height of about 10 mm.

The probe may be designed to reduce areas that cannot be easily cleaned and disinfected between uses, such as grooves or pockets of in the exterior surface of the housing. Alternatively or in combination, the probe may comprise a disposable cover configured to be placed over the housing, in order to reduce the need for cleaning and disinfecting the probe between uses. The probe is preferably configured such that its components can withstand soaking in a disinfecting solution for sterilization.

In FIG. 4C the optoacoustic probe uses the piezoceramic lead zirconate titanate ($Pb[Zr_{(x)}Ti_{(1-x)}]O_3$) ("PZT"), 2 mm thick with a 3×3 mm area.

In FIGS. 9A and 9B, the optoacoustic probe uses the piezopolymer polyvinylidene fluoride ("PVDF"), 110 µm thick with a 4×6 mm area. A specially designed miniature preamplifier is built in the probe with a bandwidth (at −3 dB level) 40 kHz<f<10 MHz.

In FIG. 13A, the optoacoustic probe uses PVDF, 110 µm thick, 6 mm diameter, with the preamplifier.

In FIG. 13E, the optoacoustic probe uses PVDF, 52 µm thick, 2×3 mm area, with the preamplifier.

In FIGS. 14A and 14B, the optoacoustic probe uses PVDF, 110 µm thick, 7 mm diameter.

In FIGS. 15A-15C, the optoacoustic probe uses PVDF, 110 µm thick, 8 mm diameter. The probe is incorporated into the small oval holder for combination with the Doppler U/S probe (Huntleigh).

In certain embodiments, the optoacoustic system includes a console unit and a handheld probe. In certain embodiments the console unit includes a controller, a processor, a photodiode array, an acoustic processing subsystem, and a cooling subsystem. The probe directs optical signals from a light source such as an optical parametric oscillator (OPO), laser diode, light emitting diode (LED), pulsed laser diode, dye laser, or solid state lasers (such as a Nd:YAG laser, Alexandrite laser) to patient tissue. The probe further comprises an acoustic transducer that receives acoustic signals generated in response to the directed light signals.

The processor may be configured to determine oxygenation of the subject in response to the measured acoustic pressure. The programmer may be programmed to provide one or more steps of the detection method, and the program may comprise program instructions stored on a computer readable memory or programmed steps of the logic circuitry such as programmable array logic or a field programmable gate array, for example. For measurement of oxygen saturation, formulas are applied to measure oxygenation when signals are good (i.e., there is low background). Theoretically, any wavelengths at which oxyhemoglobin and deoxyhemoglobin have different absorption can be used for oxygenation measurements. To measure oxygenation, at least two wavelengths are used. In certain embodiments a three-wavelength approach is utilized (760, 800, and 850 nm).

In certain embodiments, wavelengths of 760 nm and 800 nm are used. This pair is good because there is a big difference in oxy- and deoxyhemoglobin absorption spectra at 760 nm, while 800 nm is the reference point because oxy- and deoxyhemoglobin have the same absorption (isosbestic point).

In certain embodiments, the pair of wavelengths is 1064 nm and 800 nm because of a big difference of oxy- and deoxyhemoglobin absorption at 1064 nm. In still other embodiments, 760 nm and 1064 nm are utilized because at both wavelengths there is a big difference in oxy- and deoxyhemoglobin absorption.

Exemplary formulas to determine blood oxygenation at different wavelengths of light signals are listed below, where R is the ratio of optoacoustic amplitudes at 760 and 800 nm ($R=A_{760}/A_{800}$). This formula is derived from a well-known spectra of oxy and deoxyhemoglobin, while 1.54 and 0.76 are constants in the formula.

$$760\ nm: SO_2 = 1.54 - 0.76 \cdot R \rightarrow R = 2.02 - 1.31 SO_2$$

$$850\ nm: SO_2 = -2.42 + 2.66 \cdot R \rightarrow R = 0.91 + 0.38 SO_2$$

In general, for any wavelength: $R = a_i + b_i \cdot SO_2$

For instance, introducing 1.0 to generate a difference of signals would yield:

$$R - 1 = a_i + b_i \cdot SO_2 - 1$$

$$\frac{A_{760}}{A_{800}} - 1 = a_i + b_i \cdot SO_2 - 1$$

And, the differential signal $D_{760} = A_{760} - A_{800}$ may be represented by the equation:

$$\frac{A_{760} - A_{800}}{A_{800}} =$$
$$b_i \cdot SO_2 + a_i - 1 = -1.31 \cdot SO_2 + 2.02 - 1 = -1.31 \cdot SO_2 + 1.02$$

So, in general, for any wavelength, the below equation (Eq. 1) may apply:

$$\frac{A_i - A_{800}}{A_{800}} = b_i \cdot SO_2 + a_i - 1$$

And, a third wavelength (e.g. 850 nm) may be introduced to remove $A_{800}$ as follows with the following equation (Eq. 2):

$$\frac{A_{850} - A_{800}}{A_{800}} = 0.38 \cdot SO_2 + 0.91 - 1 = 0.38 \cdot SO_2 - 0.09$$

To remove $A_{800}$, Eq. 1 may be divided by Eq. 2 as follows.

$$RDS \equiv \frac{A_{760} - A_{800}}{A_{850} - A_{800}} = \frac{-1.31 \cdot SO_2 + 1.02}{0.38 \cdot SO_2 - 0.09}$$

$$(0.38 \cdot SO_2 - 0.09) \cdot (A_{760} - A_{800}) = (-1.31 \cdot SO_2 + 1.02) \cdot (A_{850} - A_{800})$$

And where $D_{760} = A_{760} - A_{800}$ and $D_{850} = A_{850} - A_{800}$ $$0.38 \cdot D_{760} \cdot SO_2 - 0.09 \cdot D_{760} = -1.31 \cdot D_{850} \cdot SO_2 + 1.02 \cdot D_{850}$$

$$0.38 \cdot D_{760} \cdot SO_2 + 1.31 \cdot D_{850} \cdot SO_2 = 1.02 \cdot D_{850} + 0.09 \cdot D_{760}$$

$$SO_2(0.38 \cdot D_{760} + 1.31 \cdot D_{850}) = 1.02 \cdot D_{850} + 0.09 \cdot D_{760}$$

$$SO_2 = \frac{1.02 \cdot D_{850} + 0.09 \cdot D_{760}}{0.38 \cdot D_{760} + 1.31 \cdot D_{850}}$$

The last above equation for $SO_2$ can be used to measure oxygenation using any (bad or good) signals with high background from hair or skin melanin. Therefore, in certain embodiments, one, two, three or more wavelengths of light signals or two or more wavelength pairs for light signals may be used to measure oxygenation optoacoustically, even in conditions of high background. The wavelengths noted above are examples only, and other wavelengths are also contemplated for use as described above and herein. The above coefficients for the various formulas and equations are examples only as well, and other coefficients for the above formulas and equations are also contemplated for use.

The console may further comprise a power supply coupled to the optical subsystem, the acoustic sensor subsystem, and the processor. The console may further comprise a display coupled to the processor to display the determined oxygenation to a user. The display may comprise a touch screen for operating the console. The console may further comprise a housing enclosing the laser diode subsystem, the acoustic sensor subsystem, and the processor. The console may further comprise a second cooling fan, which may be coupled to one or more of the processor or acoustic sensor subsystem, for cooling the console. The processor may be capable of accessing medical records of the subject.

The console may further comprise an output port for the optical source such as the laser diode subsystem and an input port for the acoustic sensor subsystem. The output port and the input port may be configured to be coupled to a sensor module or an optoacoustic probe to emit the one or more light pulses to the tissue of the subject and to receive the acoustic pressure generated in the tissue. The output port and the input port may be configured to be coupled to the sensor module or optoacoustic probe with a cable comprising one or more optical fibers.

The cooling subsystem may include a temperature controller that may include a temperature sensor to measure the temperature of the light source and a first thermoelectric cooler to add or remove heat to regulate the temperature of the light source in response to the measured temperature.

All publications, patents and patent applications cited herein are hereby incorporated by reference as if set forth in their entirety herein. While this invention has been described with reference to illustrative embodiments, this description is not intended to be construed in a limiting sense. Various modifications and combinations of illustrative embodiments, as well as other embodiments of the invention, will be apparent to persons skilled in the art upon reference to the description. It is therefore intended that the appended claims encompass such modifications and enhancements.

The invention claimed is:

1. A method for ultrasound guided optoacoustic measurement of blood oxygenation in a blood vessel comprising:
   applying an ultrasound probe to a sternal notch of a patient to thereby localize a left innominate vein,
   applying an optoacoustic system to stimulate the localized innominate vein, wherein the optoacoustic system comprises an optoacoustic stimulus and an optoacoustic probe,
   applying the optoacoustic system to the stimulated left innominate vein to detect optoacoustic signals, and
   approximating blood oxygenation at a central vena cava by quantitatively determining blood oxygenation in venous blood from the detected optoacoustic signals.

2. The method of claim 1, wherein the ultrasound probe is first removably applied to the sternal notch followed by removal of the ultrasound probe and application of the optoacoustic stimulus and probe to the sternal notch via a patient interface.

3. The method of claim 1, wherein the ultrasound probe and the optoacoustic stimulus and the optoacoustic probe are mounted together in a holder.

4. The method of claim 1, wherein applying the ultrasound probe and the optoacoustic system comprises positioning the ultrasound probe and the optoacoustic probe at the sternal notch so that axes of the probes are parallel.

5. The method of claim 1, wherein applying the ultrasound probe and the optoacoustic system comprises positioning the ultrasound probe and the optoacoustic probe at the sternal notch so that axes of the probes are at an angle to each other.

6. The method of claim 1, wherein the ultrasound probe and the optoacoustic probe are housed in a single device.

7. The method of claim 1, wherein applying the optoacoustic system comprises applying the optoacoustic stimulus with at least a pair of wavelengths selected from: 760 nm and 800 nm; 1064 nm and 800 nm; and 760 nm and 1064 nm.

8. The method of claim 1, further comprising:
   using the approximated blood oxygenation at the central vena cava to diagnose that the patient is in shock and/or in danger of a traumatic brain injury; and
   providing resuscitation therapy to the patient that is in shock and/or in danger of traumatic brain injury.

9. The method of claim 1, wherein the optoacoustic system comprises a light source selected from an optical parametric oscillator (OPO), laser diode, light emitting diode (LED), pulsed laser diode, dye laser, or solid state laser.

10. The method of claim 1, wherein the optoacoustic system comprises a laser diode-based system with a high pulse repetition rate.

11. The method of claim 1, further comprising, using a force transducer that is attached to a surface of the optoacoustic probe to measure an amount of force being applied to the optoacoustic probe, wherein a set amount of force is required for an optimal signal to be obtained from the optoacoustic probe.

* * * * *